United States Patent [19]
Houck et al.

[11] Patent Number: 5,954,954
[45] Date of Patent: Sep. 21, 1999

[54] METHOD AND APPARATUS FOR DETERMINATION OF ANALYTE CONCENTRATION

[75] Inventors: Raymond K. Houck, Oakmont; Douglas J. Koebler, Irwin; Glen P. Williams, Springdale; Joseph M. Levy, Gibsonia; Victor G. Danielson, Harrison City, all of Pa.

[73] Assignee: Suprex Corporation, Pittsburgh, Pa.

[21] Appl. No.: 08/879,336

[22] Filed: Jun. 20, 1997

Related U.S. Application Data

[60] Division of application No. 08/388,274, Feb. 13, 1995, Pat. No. 5,750,029, which is a continuation-in-part of application No. 07/962,463, Oct. 16, 1992, abandoned.

[51] Int. Cl.⁶ .................................................. B01D 15/08
[52] U.S. Cl. ..................... 210/198.2; 210/511; 210/634; 210/656; 210/659; 422/256; 422/261; 422/285
[58] Field of Search ..................... 210/634, 635, 210/656, 659, 137, 198.2, 511; 251/129.15, 331, 335.2; 422/256, 261, 285

[56] References Cited

U.S. PATENT DOCUMENTS

| | | | |
|---|---|---|---|
| 3,853,157 | 12/1974 | Madaio | 141/2 |
| 4,239,623 | 12/1980 | Schrenker | 210/96.1 |
| 4,614,661 | 9/1986 | White | 426/511 |
| 4,728,434 | 3/1988 | Trafford | 210/101 |
| 4,892,654 | 1/1990 | Nickerson | 210/198.2 |
| 5,009,778 | 4/1991 | Nickerson | 210/659 |
| 5,268,103 | 12/1993 | Jameson | 210/634 |
| 5,372,716 | 12/1994 | Levy | 210/634 |
| 5,614,089 | 3/1997 | Allington | 210/634 |
| 5,750,027 | 5/1998 | Allington | 210/634 |

FOREIGN PATENT DOCUMENTS

| | | | |
|---|---|---|---|
| 0052078 | 5/1982 | European Pat. Off. | 210/198.2 |
| 3016917 | 11/1981 | Germany | 210/198.2 |

OTHER PUBLICATIONS

Snyder, Introduction to Modern Liquid Chromatography, 1979, John Wiley & Sons, Inc, New York pp. 92–94 and 393–394.

Mikes' Laboratory Handbook of Chromatographic and Allied Methods, John Wiley & Sons, Inc., New York, 1979, pp. 440 & 445.

*Primary Examiner*—Ernest G. Therkorn
*Attorney, Agent, or Firm*—Ansel M. Schwartz

[57] ABSTRACT

The present invention pertains to an apparatus for gathering analyte. The apparatus comprises a pumping mechanism for pumping solvent at supercritical pressure. The apparatus also comprises an extraction mechanism which receives a first sample and at least a second sample separate and distinct from the first sample and extract analyte from them essentially simultaneously. The extraction mechanism is connected to the pump mechanism to receive solvent at supercritical pressure for extracting the analyte from the samples. The apparatus additionally comprises a collection mechanism for collecting analyte from the solvent after the analyte has been extracted from the samples. The collection mechanism receives the supercritical solvent having the analyte extracted from the samples from the extraction mechanism. The present invention pertains to a method for extracting analyte. The method comprises the steps of pumping solvent at a supercritical pressure. Then there is the step of extracting analyte from N samples essentially simultaneously with the solvent at a supercritical pressure, where N is greater than or equal to two and is an integer. The N samples are separate and distinct from each other. Then there is the step of collecting the analyte of the N samples from the solvent.

22 Claims, 20 Drawing Sheets

METHOD AND APPARATUS FOR DETERMINATION OF ANALYTE CONCENTRATION

This is a divisional of application(s) Ser. No. 08/388,274 filed on Feb. 13, 1995, now U.S. Pat. No. 5,750,029, which, in turn, is a continuation-in-part of Ser. No. 07/962,463, filed Oct. 16, 1992, now abandoned.

FIELD OF THE INVENTION

The present invention is related to supercritical fluid extraction. More specifically, the present invention is related to supercritical fluid extraction of fat from a plurality of samples so the fat content of the sample can be determined.

BACKGROUND OF THE INVENTION

Supercritical fluid extraction (SFE) is a sample preparation technique used to extract analytes of interest from a sample, for example, fat from a food sample. Some type of sample preparation must be performed for a wide range of environmental, food, polymer, petroleum, pharmaceutical and other classes of samples due to the complex nature of the samples. Many of these samples are so complex that they cannot be directly analyzed by analytical techniques such as gas chromatography (GC) or liquid chromatography (LC). The complex samples must first go through a sample preparation step to perform a gross separation of the analytes of interest from the sample matrix in which they are contained, for example, the environmental pollutants from soil. After the sample preparation step, then just the analytes of interest are analyzed by the analytical technique such as gas chromatography (GC), liquid chromatography (LC), or supercritical fluid chromatography (SFC). Other analytical techniques could be used such as mass spectroscopy (MS) or nuclear magnetic resource (NMR).

The most popular sample preparation steps are Soxhlet extraction and liquid extraction. An alternative to these types of extraction techniques is supercritical fluid extraction (SFE). SFE offers a relatively rapid, simple and inexpensive technique to perform sample preparations. The basis of SFE is that a fluid, such as carbon dioxide, is held at a specific pressure, temperature and flowrate, which is above its critical temperature and pressure and thus is a supercritical fluid. The supercritical fluid is passed through the sample matrix containing the analytes of interest. This sample matrix is contained in an extraction vessel. The fluid diffuses into the pores of the matrix, solubilizes the analytes of interest, and then carries the analytes away from the matrix. The analytes are then collected by some device, so that the analytes can be analyzed by some further analytical technique, such as chromatography. The matrix (now without analytes) is left behind in the extraction vessel. Supercritical fluids have favorable diffusivities and viscosities providing for good mass transfer characteristics. Their solvent strength can be easily controlled by changing fluid pressure or temperature. These are but a few of the advantages of supercritical fluid extraction.

Typically, an SFE system is comprised of a pump which pumps the supercritical fluid to an extraction vessel where analytes are extracted from a sample matrix. The analytes are then transported to a collection device where the supercritical fluid is depressurized to ambient pressure and is vented. The analysis of the collected analytes can be either "off-line", that is, remote from the extraction and/or collection device, or "on-line", that is, fluidically connected to the extraction and/or collection device.

The primary supercritical fluid used in SFE is carbon dioxide due to its low pressure and temperature critical points (71 atm, 31° C., respectively) and its ability to solubilize nonpolar or moderately polar analytes. When it is desired to extract a polar analyte, then it is well known in the art to employ a co-solvent with the carbon dioxide. These co-solvents are typically referred to as modifiers or entrainers and are typically a liquid organic solvent such as methanol, ethanol, propylene carbonate, acetone, tetrahydrofuran, fomic acid, etc. that are blended with the carbon dioxide in 1 to 80% by volume or mole percent to form a mixture that retains much of the diffusion characteristics of the pure carbon dioxide phase but that has a much higher polarity and thus is able to solubilize polar analytes and extract the polar analytes from the sample matrix.

Supercritical fluid extraction (SFE) has been utilized for some time in the extraction of fats and lipids in various matrices. Stahl, et al., [E. Stahl, K. W. Quirin, D. Gerard. Verdichtete Gas zur Extraktion und Raffination. Springer-Verlag Heidelberg (1987)] used supercritical $CO_2$ for the extraction and refining of oils seeds. Froning, et al. [G. W. Froning, R. L. Wehling, S. L. Cuppett, M. M. Pierce, L. Niemann. D. Siekman, J. Food Sci. 55, 95 (1990)] have extracted cholesterol and other triglycerides from egg powder. King, et al. [J. W. King, J. H. Johnson, J. P. Friedrich. J. Agric. Food Chem. 37, 951 (1989); J. W. King, J. H. Johnson, Fifth International Symposium on SFC and SFE, (Jan. 10–14, 1994)] used SFE on dehydrated foods and meats to extract free lipid fractions and total fat. Lembke and Engelhardt [P. Lembke, H. Engelhardt, Fifth International SFE/SFC Symposium, (Jan. 10–14, 1994); H. Engelhardt, P. Lembke, Chromatographia, 34, 509 (1993)] recently used SFE for total fat determinations in cheese and meat sample matrices, using a pre-extraction acid treatment of the sample to enhance the accessibility of the lipids that were associated with carbohydrates and proteins in those sample matrices.

Recently, the accurate labeling requirements for fat in foods has been revised by federal agencies (FDA and USDA). This is a result of the Nutrition Labeling and Education Act which requires the labeling of total, saturated and unsaturated fats packaged in foods [M. Clemmitt, Scientist, 8, (Nov. 1991)]. In addition, food manufacturers also require the consistent determination of fat for quality control purposes.

Presently, these determinations are performed by such techniques as Soxhlet (i.e., petroleum ether) extractions, the Roese-Gottlieb method (for milk products), or one of several acid hydrolysis steps followed by liquid solvent extraction. Attempts to eliminate the use of toxic, flammable solvents, to reduce conventional extraction times (i.e., 12–16 hours), and to have an independent monitor of fat levels has prompted food manufacturers to search for alternative methods. For example, near infrared spectroscopy has been used for fat determinations in food stuffs, but requires frequent calibrations and updating. SFE is practical alternative for fat determinations. By employing non-toxic, non-flammable solvents, namely supercritical carbon dioxide ($CO_2$), SFE can be used, due to the physical properties of supercritical fluids, to yield precise and rapid fat extractions eliminating the need for liquid solvent disposal. Moreover, due to recent instrumental developments, especially in decompression control, SFE can be performed reliably and in a very straight forward, routine fashion. This kind of ease of operation is important, for example, for food manufacturing plant laboratories. For instance, supercritical fluid extraction has been utilized for the gravimetric determination of fats in snack foods (i.e. potato chips, tortilla chips, corn chips, popcorn).

With supercritical carbon dioxide ($CO_2$), fats can be extracted in less than one hour in a reproducible fashion, either manually or sequentially automated.

SUMMARY OF THE INVENTION

The present invention pertains to an apparatus for gathering analyte. The apparatus comprises a pumping mechanism for pumping solvent at supercritical pressure. The apparatus also comprises an extraction mechanism which receives N samples and extracts analyte from them essentially simultaneously. The N samples are separate and distinct from each other, where $N \geq 1$ and is an integer. The extraction mechanism is connected to the pump mechanism to receive solvent at supercritical pressure for extracting the analyte from the samples. The apparatus additionally comprises a collection mechanism for collecting analyte from the solvent after the analyte has been extracted from the samples. The collection mechanism receives the supercritical solvent having the analyte extracted from the samples from the extraction mechanism.

The present invention pertains to a method for extracting analyte. The method comprises the steps of pumping solvent at a supercritical pressure. Then there is the step of extracting analyte from N samples essentially simultaneously with the solvent at a supercritical pressure, where N is greater than or equal to two and is an integer. The N samples are separate and distinct from each other. Then there is the step of collecting the analyte of the N samples from the solvent.

The present invention pertains to an apparatus for extracting analyte. The apparatus comprises a pump mechanism for pumping solvent at supercritical pressure. The apparatus comprises an extraction mechanism which receives a sample. The extraction mechanism is connected to the pump mechanism to receive the solvent at supercritical pressure from the pump mechanism for extracting analyte from the sample. There is a collection mechanism for collecting analyte from the solvent after the analyte has been extracted from the sample. The collection mechanism receives the supercritical solvent having the analyte extracted from the sample from the extraction mechanism. The apparatus also comprises a valving mechanism connecting the pumping mechanism and the collection mechanism with the extraction mechanism. The valving mechanism controls the flow of the solvent to the extraction mechanism and provides solvent to the extraction mechanism at least twice in a static state and twice in the dynamic state. Preferably, the valving mechanism includes a first valve connected to the pump. The first valve directs solvent from the pump to the extraction mechanism when the first valve is in a first state and shuts off the solvent from the pump to the extraction mechanism when the first valve is in a second state. There is also a third valve connected to the extraction mechanism and the collection mechanism. The third valve directs solvents from the extraction mechanism to the collection mechanism when the third valve is in a first state, and stops solvent from flowing from the extraction mechanism when the third valve is in a second state. The collection mechanism preferably includes a restrictor for reducing the supercritical pressure of the solvent to below supercritical pressure. The restrictor is connected to the third valve. The The apparatus can include means for providing modifier to the supercritical solvent. The modifier providing means is connected to the valving mechanism. The modifier providing means preferably includes a plurality of modifier pump mechanisms for providing a plurality of different modifiers connected to the valving mechanism. Each pump mechanism provides a corresponding modifier to the supercritical solvent through the valving mechanism. Preferably, the plurality of modifier pumps are disposed in parallel and connected to the valving mechanisms to provide tertiary and quaternary supercritical solvent and modifier mixtures to the extraction mechanism. The valving mechanism preferably includes a modifier tee connected to the modifier mechanisms through which modifier is introduced to the supercritical solvent. Preferably, the valving mechanism preferably includes a check valve disposed between the pumping mechanism and the tee. The check valve prevents modifiers from back flowing to the pumping mechanisms from the modifier providing means. Preferably, each modifier pumping mechanism includes a modifier supply having corresponding modifiers. Preferably, there is a computer controlling the modifier pumping mechanisms. The computer is connected to the modifier pumping mechanisms. Alternatively, the modifier providing means can include a multi-headed modifier pump mechanism to provide multicomponent modifier to the supercritical solvent. The multi-headed modifier pump mechanism is connected with the valving mechanism. The multi-headed modifier pump mechanism preferably is a dual-headed, triple-headed or four-headed modifier pump having dual, triple or quadruple modifier supplies, respectively, connected to the respective pumps.

The present invention pertains to a method for gathering analyte. The method comprises the steps of flowing solvent at a supercritical pressure to a sample. Then there is the step of holding the solvent at the sample for a predetermined time so analyte in the sample is gathered by the solvent. Next, there is the step of flowing the solvent away from the sample. Then, there is the step of reducing the supercritical pressure of the solvent to below supercritical pressure. Next, there is the step of collecting analyte from the solvent. Then, there is the step of flowing solvent at a supercritical pressure to the sample. Next, there is the step of holding the solvent at the sample for a predetermined time so analyte in the sample is gathered by the solvent. Next, there is the step of flowing the solvent away from the sample. Then, there is the step of reducing the supercritical pressure of the solvent to below supercritical pressure. Next there is the step of collecting analyte from the solvent. The flowing supercritical solvent step preferably includes the step of mixing modifier into the solvent. The mixing step can include the step of pumping a desired modifier of a plurality of modifiers into the solvent. Alternatively, the mixing step can include the step of pumping multicomponent modifier from a combination of modifiers into the solvent.

The present invention pertains to a method for processing a sample. The method comprises the step of flowing supercritical solvent through a sample in a chamber. Then, there is the step of heating the sample to above 80° C. Next, there is the step of venting the chamber while heating the sample a predetermined time to evaporate the solvent out of the sample.

The present invention pertains to an apparatus for extracting analyte. The apparatus comprises a pump mechanism for pumping solvent at supercritical pressure. There is an extraction mechanism which receives a sample. The extraction mechanism is connected to the pump mechanism to receive the solvent at supercritical pressure from the pump mechanism for extracting analyte from the sample. There is a collection mechanism for collecting analyte from the solvent after the analyte has been extracted from the sample. The collection mechanism receives the supercritical solvent having the analyte extracted from the sample from the extraction mechanism. The apparatus also comprises a purge mechanism for removing moisture from the sample. The purge mechanism is connected to the extraction mechanism. The purge mechanism preferably includes an inert gas supply for providing inert gas to the extraction mechanism to displace moisture in the sample. The purge mechanism preferably includes a first valve mechanism disposed between and connected to the pumping mechanism and the extraction mechanism. The inert gas supply is connected to the first valve mechanism. The first valve mechanism allows inert gas to flow from the inert gas supply to the extraction mechanism and solvent from the pumping mechanism from flowing to the extraction mechanism when the first valve mechanism is in a first state. The first valve mechanism stops the flow of inert gas from the inert gas supply to the injection mechanism when the first valve mechanism is in a second state. The extraction mechanism preferably includes a heating mechanism which heats the sample a desired amount while the inert gas flows through the extraction mechanism having the sample. The first valve mechanism preferably includes a first valve connected to the pumping mechanism and the extraction mechanism, and a purge valve mechanism having an open and closed state connected to the first valve. The first valve allows solvent to flow to the extraction mechanism when the first valve is in the first state. The first valve in a second state stops solvent from flowing to the extraction mechanism. The first valve in a third state flowing inert gas from the inert gas supply to the extraction mechanism when the purge valve mechanism is in the open state. The purge valve mechanism preferably includes a purge valve having an open and a closed state. There is a purge tee connected to the purge valve and the first valve and a vent valve having an open and closed state connected to the tee. The inert gas from the inert gas supply flows to the first valve when the purge valve is in an open state and the vent valve is in a closed state. Preferably, the heating mechanism heats the sample to more than 80° C. The inert gas supply provides inert gas at a pressure preferably between 20 and 300 P.S.I.

The present invention pertains to an apparatus for extracting analyte. The apparatus comprises a pump mechanism for pumping solvent at supercritical pressure. There is an extraction mechanism which receives a sample. The extraction mechanism is connected to the pump mechanism to receive the solvent at supercritical pressure from the pump mechanism for extracting analyte from the sample. There is a collection mechanism for collecting analyte from the solvent after the analyte has been extracted from the sample. The collection mechanism receives the supercritical solvent having the analyte extracted from the sample from the extraction mechanism. There is a precooler system for cooling solvent for supercritical extraction prior to the solvent being pumped by the pumping mechanism. The precooler system is connected to the pumping mechanism. The precooler system preferably comprises a super cooler assembly for cooling the solvent. The super cooler assembly is connected to the pumping mechanism. Also, there is a pump head cooler assembly connected to the pumping mechanism for cooling the pumping mechanism during operation of the pumping mechanism. The super cooler assembly preferably includes at least one thermo electric cooler having a cold side which is in thermal contact with the solvent and a hot side having a fan which expels heat from the thermo electric cooler. The precooler system preferably includes a tube coil in thermal contact with a tube coil through which the solvent flows through the thermo electric cooler. Preferably, the pumping mechanism has a pump head and the pump head cooler assembly includes a heat sink, and a thermally conductive bracket in contact with the pump head through which heat from the pump head escapes to the heat sink. The heat sink preferably includes a first and a second fan.

The present invention pertains to an extraction mechanism for extracting analyte from a sample. The extraction mechanism comprises an extraction vessel which holds a sample. The extraction mechanism also comprises a plunger assembly which holds the vessel and penetrates into the vessel to introduce and remove solvent from the vessel. The plunger assembly has a plunger which moves up and down to penetrate into and separate from the vessel. The plunger assembly preferably includes a spring mechanism for placing the plunger in a stable position. The spring mechanism is connected to the plunger. The plunger assembly preferably includes a forcing mechanism which moves the plunger into the vessel, and the spring mechanism retracts the plunger from the vessel when the forcing mechanism is deactivated. The plunger assembly preferably includes a plate connected to the plunger and against which the spring mechanism presses. The plate is connected to the forcing mechanism which pushes against the plate and compresses the spring mechanism so the plunger penetrates the vessel when the forcing mechanism is activated. The forcing mechanism preferably includes a hydraulic system. The hydraulic system preferably includes a hydraulic cylinder connected to the plate and a hydraulic pump which pumps hydraulic fluid to the hydraulic cylinder to expand the hydraulic cylinder and move the plate. Alternatively, the spring mechanism preferably holds the plunger in the vessel. The extraction mechanism can then include a plate in contact with the plunger and the spring mechanism. The spring mechanism preferably pushes down on the plate causing the plunger to penetrate into the vessel. The extraction mechanism preferably also includes a plunger top extending perpendicularly from the plunger which a user lifts to insert the vessel below the plunger.

The present invention pertains to a restrictor for flow of supercritical solvent. The restrictor comprises a housing having a central chamber and a first port, second port and third port connected to the central chamber. There is a high pressure tube connected to the first port which delivers supercritical solvent to the chamber through the first port. There is an actuator mechanism connected to the second port. There is a needle connected to the actuator mechanism. The needle extends from the actuator mechanism through the chamber and through the third port. The actuator mechanism moves the needle to maintain a desired flow of supercritical solvent out the third port. The needle has a needle end. Additionally, the restrictor is comprised of an outlet tube which is connected to the third port and extends from the third port. The outlet tube surrounds the needle. The outlet tube has an opening which conforms with the needle and to control the flow of solvent out the third port and the change in pressure of the solvent. The needle end and outlet tube opening is remote from the housing. The restrictor preferably includes a solvent flush mechanism connected to the third port to provide solvent flush to the chamber and third port to clear them of solvent. Preferably, the housing includes a fourth port. The restrictor preferably includes a solvent flush mechanism connected to the fourth port to provide solvent flush to the chamber and third port to clear them of solvent and analyte. The restrictor preferably includes a heating mechanism adjacent to the needle end and the tube outlet opening to heat the outlet opening and needle end so solvent or analyte does not clog the outlet tube opening. The solvent flush mechanism preferably includes solvent flush tubing connected to the fourth port of the housing, and a solvent flush pump connected to the tubing to pump the solvent flush to the fourth port. The solvent flush mechanism preferably includes a solvent flush check valve disposed in the solvent flush tubing to prevent solvent from the first port flowing through the solvent flush tubing. The solvent flush check valve is disposed between the housing and the solvent flush pump. There can also be a solvent flush supply connected to the solvent flush pump. The actuator mechanism preferably includes an actuator. The actuator mechanism preferably includes an actuator, and the restrictor preferably includes a control mechanism for controlling the movement of the actuator to move the needle end relative to the outlet opening. The restrictor preferably includes a ferrule disposed in the second outlet between the actuator and the chamber. The needle extends through the ferrule. The ferrule seals the second outlet so solvent from the first outlet cannot flow into the second outlet. The control mechanism preferably includes a motor mechanism to move the actuator to move the needle and a computer mechanism for instructing the motor mechanism how to move the actuator to move the needle. The computer mechanism is connected to the solvent flush pump to control when the solvent pump operates. The motor mechanism preferably includes a stepper motor connected to the actuator to move the actuator, and a stepper motor driver connected to the stepper motor and to the control mechanism to drive the stepper motor. The control mechanism preferably includes a computer to determine how to move the actuator, and a central microprocessor connected to the stepper motor driver and the solvent flush pump for controlling their operation. The solvent flush is preferably methanol, methylene chloride, acetone or hexane. The heating mechanism preferably includes an inductive heating mechanism, a cartridge heater providing conductive heat, a hot air convection heater, or a microwave heater. In one embodiment, the needle end is flared radially outward from the needle axis, and the outlet tube opening has a shape which conforms with the flared end of the needle end. In another embodiment, the needle end is a point and the point defines a seating surface, and the outlet tube opening conforms with the point of the needle end. The outlet tube opening is defined by an outlet tube seating surface on the interior of the outlet tube. The restrictor can include a collector connected to the outlet tube opening. The collector is preferably comprised of an analyte trap, a solvent trap, or a waste vial. The restrictor can include a chromatograph having an inlet port to which the outlet tube is connected. The chromatograph can be a gas, liquid or supercritical chromatograph. The restrictor can be connected to an infrared detection device or a mass spectrometer which is coupled to the outlet tube.

The present invention pertains to an apparatus for identification of a sample. The apparatus comprises a supercritical fluid chromatograph which produces an outflow from a chromatograph outlet. There is a variable restrictor having an inlet port coupled with the chromatograph outlet to receive the outflow. The restrictor has an outlet tube with an opening. The tube extends from the housing. The restrictor has a needle disposed in the outlet tube with a needle end that conforms with the outlet tube opening and controls the flow of outflow and its change of pressure. The restrictor has an actuator which moves the needle a desired amount. The needle end and outlet tube opening are remote from the housing. The apparatus also comprises a detector connected with the outlet and the needle end to receive outflow from the outlet tube. Preferably, the detector is a flame ionization detector, nitrogen phosphorous detector, ultraviolet detector or mass spectrometer.

The present invention pertains to a method for restricting flow of supercritical fluid. The method comprises the step of flowing supercritical solvent through a housing into an outlet tube having an outlet tube opening. Then there is the step of moving an end of a needle disposed in the outlet tube relative to the outlet tube opening to control the flow of solvent out of the outlet tube and change of pressure of the solvent as it flows out of the outlet tube. The outlet tube opening and needle end are remote from the housing. Preferably, after the moving step, there is the step of flushing the solvent out of the outlet tube. The flushing step can include the step of pumping solvent flush through the outlet tube. Alternatively, the flushing step can include the step of immersing the needle end and outlet tube opening into a solvent cleanser. Alternatively, the flushing step includes the steps of inserting the outlet tube opening and needle end into a tee; and pumping solvent flush into the tee to wash the needle end and outlet tube opening. After the moving step, there is preferably the step of introducing the solvent into a collector. Alternatively, after the moving step, there is the step of flowing the solvent into a detector to identify what is in the solvent.

The present invention pertains to a method for identifying a sample. The method comprises the steps of producing an outflow having analyte of the sample from a supercritical chromatograph. Then there is the step of flowing the outflow into an outlet tube having an outlet tube opening. Next there is the step of moving an end of a needle disposed in the outlet tube relative to the outlet tube opening to control the flow of the outflow out of the outlet tube and change of pressure of the outflow as it flows out of the outlet tube. The outlet tube opening and needle end are remote from the housing. Then, there is the step of providing the outflow from the outlet tube opening to a detector to which the outlet tube opening is connected.

The present invention pertains to a method for determining fat in food. The method comprises the step of extracting fat from the sample. Then there is the step of identifying the percent fat in the sample. Before the extracting step, there is preferably the step of weighing the sample. The identifying step preferably includes the step of weighing the sample after the fat has been extracted from the sample. The identifying step preferably includes after the step of weighing the sample after the extracting step, the step of comparing the weight of the sample after the extraction of fat from the sample with the weight of the sample before the extraction. Preferably, before the extracting step, there is the step of adding an absorbent to the sample to retain water if the sample has a water content greater than 2%. Before the extracting step, there is preferably the step of adding modifier to the sample. Preferably, before the extracting step, there is the step of grounding up the sample. After the extracting step, there is preferably the step of heating the sample to purge the sample of entrapped solvent. After the extracting step, there is preferably the step of collecting the fat. The identifying step preferably includes the step of identifying the constituents of the fat. Alternatively, before the extracting step, there is the step of weighing the sample and the extraction vessel the sample is in. The identifying step includes the steps of weighing the extraction vessel with the sample after fat has been extracted from the sample, and comparing the weight of the sample and the extraction vessel before the extracting step and with the weight of the sample and the extraction vessel after the extracting step. Before the extracting step, there is the step of weighing the sample to obtain the sample weight, and a collection vial to receive extracted fat from the sample to obtain the weight of collection vial. Before the identifying step, there is the step of collecting the fat from the sample in the collection vial. The identifying step includes the steps of weighing the collection vial with the fat, and comparing the weight of the collection vial with the fat with the weight of the sample before the extracting step.

The present invention pertains to an apparatus for extracting analyte. The apparatus comprises a pump mechanism for pumping solvent at supercritical pressure. There is an extraction mechanism which receives N samples and extracts analyte from the N samples essentially simultaneously, where N≧2 and is an integer, said N samples separate and distinct from each other. The extraction mechanism is connected to the pump mechanism to deliver solvent at supercritical pressure for extracting the analyte from the samples. The extraction mechanism includes an extraction chamber. The chamber is connected to receive solvent at a supercritical pressure from the pumping mechanism and connected to the restrictor to pass solvent to it. There is a first extraction vessel which holds the first sample and a second extraction vessel which holds the second sample. The first and second vessels are disposed in the extraction chamber. Preferably, there is means for heating the extraction chamber to heat the first and second vessels.

The present invention pertains to a disposable seal for an extraction vessel for supercritical extraction. The seal comprises a top layer. There is a middle layer in contact with the top layer. Also, there is a bottom layer in contact with the middle layer. Preferably, the top and bottom layer each have a hole. The top and bottom layer are each preferably about 0.02–0.03 inches thick and the middle layer is about 0.1 inches thick. The top and bottom layers are made of acetal and the middle layer is made of filter paper.

The present invention pertains to an extraction apparatus for supercritical fluid extraction. The apparatus comprises an extraction vessel having at least one opening through which supercritical fluid flows. There is also a 1-time use disposable seal disposed over the one opening.

The present invention pertains to a method for supercritical fluid extraction. The method comprises the steps of placing a disposable seal over an opening of an extraction vessel. The extraction vessel has a sample in the extraction vessel. Then, there is the step of flowing supercritical fluid through the extraction vessel and the seal. Next there is the step of removing the disposable seal from the vessel. Preferably after the removing step, there are the steps of placing another sample into the vessel. Then, there is the step of placing another disposable seal over the opening of the vessel. Next, there is the step of flowing supercritical fluid through the extraction vessel and the other seal.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
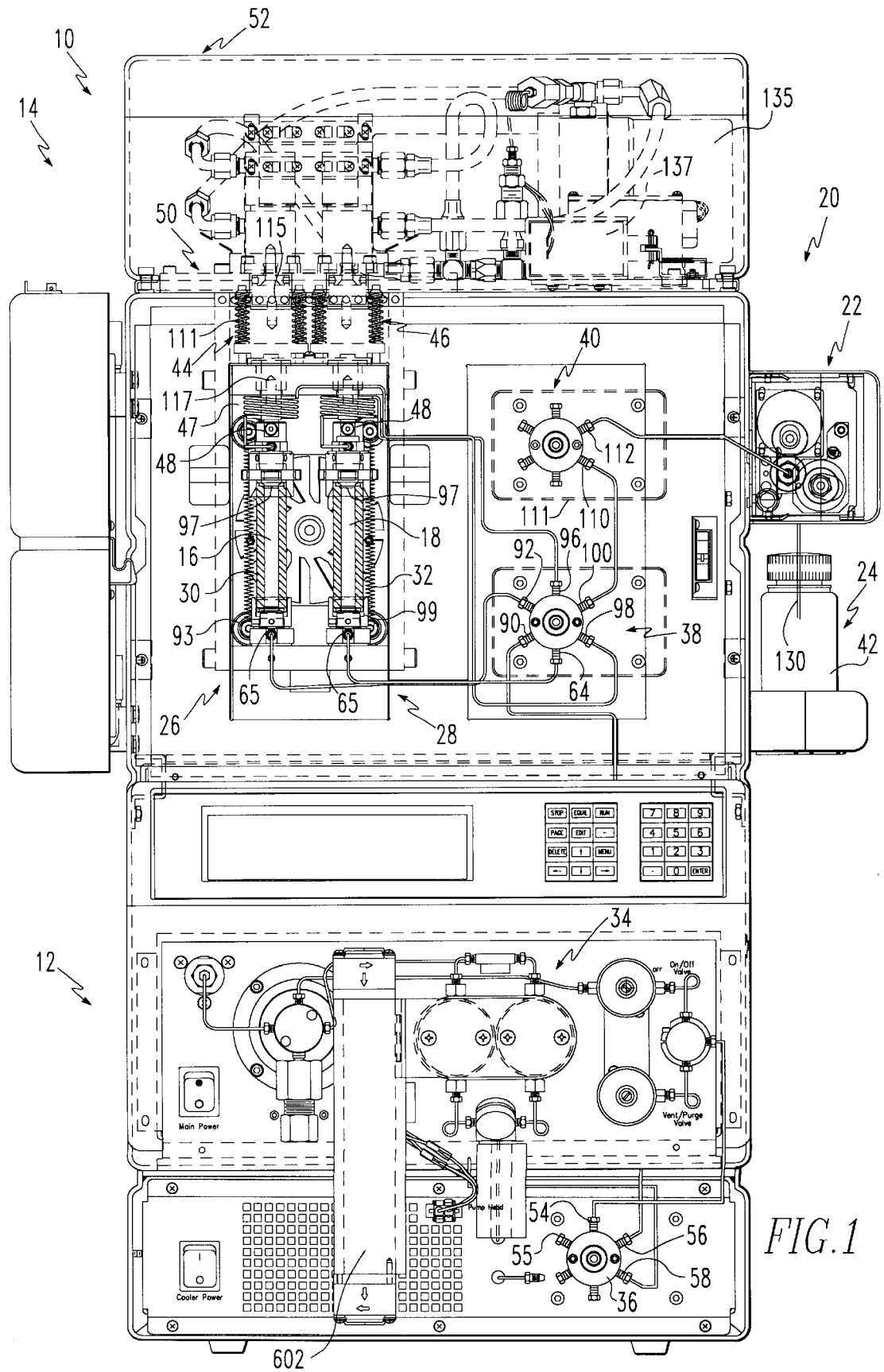
FIG. 1 is a schematic representation of an apparatus for collecting analyte of the present invention.

Referring now to the drawings wherein like reference numerals refer to similar or identical parts throughout the several views, and more specifically to FIG. 1 thereof, there is shown an apparatus 10 for gathering analyte. The apparatus 10 comprises a pumping mechanism 12 for pumping solvent at supercritical pressure. The apparatus 10 also comprises an extraction mechanism 14 which receives N samples and extracts analyte from them essentially simultaneously, where N≧1 and is an integer. The N samples are separate and distinct from each other. The extraction mechanism 14 is connected to the pump mechanism 12 to receive solvent at supercritical pressure for extracting the analyte from the samples. The apparatus 10 additionally comprises a collection mechanism 20 for collecting analyte from the solvent after the analyte has been extracted from the samples. The collection mechanism 20 receives the supercritical solvent having the analyte extracted from the samples from the extraction mechanism 14.

Preferably, the collection mechanism 20 includes a restrictor 22 connected to the extraction mechanism 14 which receives the solvent with analyte at a supercritical pressure and converts it to a pressure of 10 atmospheres or less. The restrictor 22 preferably is a variable restrictor. The collection mechanism also preferably includes a collector 24 in communication with the restrictor 22 which collects analyte in the solvent. The collector 24 preferably includes a vial 42 that collects the analyte and allows the solvent to disperse into the atmosphere.

The collection mechanism 20 preferably includes a third valve 40 connected to the restrictor 22 and connected to the extraction mechanism 14. The third valve 40 directs solvent from the extraction mechanism 14 to the restrictor 22 when the third valve 40 is in a first state, and stopping solvent from flowing from the extraction mechanism 14 when the third valve 40 is in a second state. Preferably, the second valve 38 receives solvent from the first extraction chamber 26 and directs it to the third valve 40 when the second valve 38 is in the first state and receives solvent from the second extraction chamber 28 and directs it to the third valve 40 when the second valve 38 is in the second state.

Valves 40, 38 and 36 are "2 way switching" valves. This means that these valves can switch the flow from one inlet valve port to two adjacent valve outlet ports. Thus the valves can be in either of two states, depending upon which outlet port the inlet port is connected. For the method shown in FIG. 1, the valve states are:

| Valve # | State | State | Ports that are connected |
| --- | --- | --- | --- |
| Valve 40 | Static | 2nd state | 110 to 111 |
|  | Dynamic | 1st state | 110 to 112 |
| Valve 38 | A | 1st state | 90 to 92, 96 to 100, 98 to 64 |
|  | B | 2nd state | 90 to 64, 92 to 96, 98 to 100 |
| Valve 36 | PM-Pump | 1st state | 54 to 56 |
|  | Vent-Vent | 2nd state | 56 to 58, 54 to 55 |

The extraction mechanism 14 preferably includes a first extraction chamber 26 and at least a second extraction chamber 28. Each chamber is connected to receive solvent at a supercritical pressure from the pumping mechanism 12, and connected to the restrictor 22 to pass solvent to it. The extraction mechanism 14 preferably also includes a first extraction vessel 30 which holds a first sample 16. The first extraction vessel 30 is disposed in the first extraction chamber 26. There is also a second extraction vessel 32 which holds a second sample 18. The second extraction vessel 32 is disposed in the second extraction chamber 28. The extraction mechanism 14 also consists of a thermal zone 47 which encompasses extraction chambers 26 and 28 and heats these extractions chambers.

The extraction mechanism 14 preferably includes a first plunger assembly 44 in movable contact with the first extraction chamber 26 which connects with the first extraction chamber 26 and seals the first extraction vessel 30 when analyte is extracted from the first sample 16. The first plunger assembly 44 is in fluidic communication with the second valve 38 so solvent in the first extraction vessel chamber 26 can flow to the second valve 38 through the first plunger assembly 44. The extraction mechanism 14 preferably also includes a second plunger assembly 46 in movable contact with the second extraction chamber 28 which connects with the second extraction chamber 28 and seals the second extraction vessel 32 when analyte is extracted from the second sample 18. The second plunger assembly 46 is in fluidic communication with the second valve 38 so solvent in the second extraction chamber 28 can flow to the second valve 38 through the second plunger assembly 46.

Preferably, the first and second plunger assemblies 44 and 46 each are comprised of a plunger 48, a spring mechanism 50 in which the plunger 48 is seated and a forcing mechanism 52 which moves the plunger 48. The restrictive plunger 48 penetrates into and seals the respective extraction vessel when the forcing mechanism 52 forces the respective plunger 48 into the respective vessel, and the spring mechanism 50 retracts the respective plunger 48 from the respective extraction vessel when the forcing mechanism 52 is deactivated. Preferably, each plunger is in fluidic communication with the second valve 38 so solvent in the respective extraction chamber can flow to the second valve 38 through the respective plunger.

In FIG. 1, the clamping assembly is spring loaded up. A set of springs 111 press against plate 115 holding it up. Plate 115 is directly connected to the plunger 48 through rod 117. In normal operation, the springs 111 cause the plunger 48 to be in the "up" position. A vessel can be inserted by the user and then the forcing mechanism 52 drives the plate 115 and thus the plungers 48 downward to engage and seal the vessels.

Figure 11:
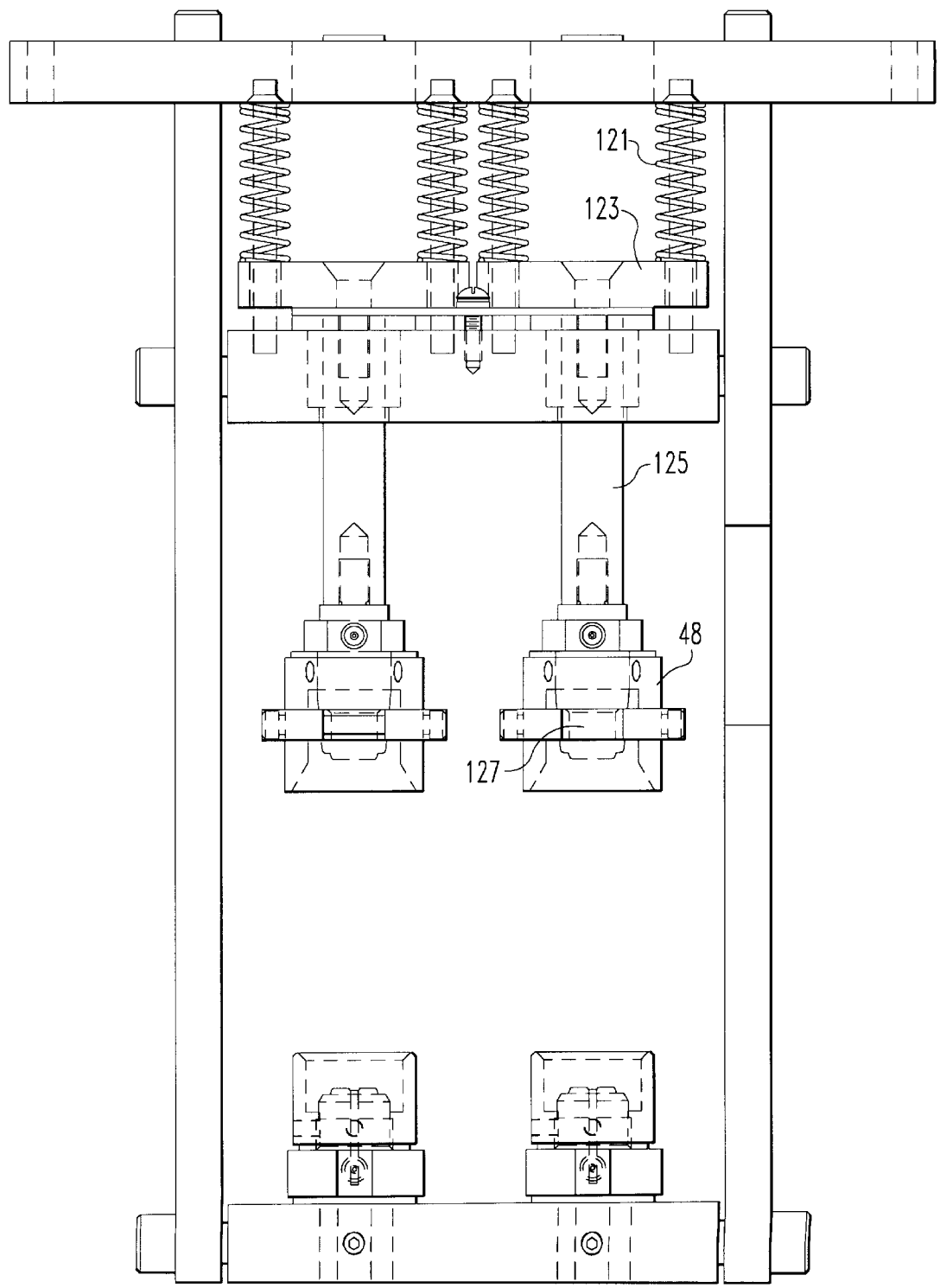
FIG. 11 is a schematic representation of a portion of the extraction mechanism.

An alternative to the vessel clamping assembly is shown in FIG. 11. In FIG. 11, the clamping assembly is spring loaded down. A set of springs 121 press against plate 123 holding it down. Plate 123 is directly connected to the plunger 48 through rod 125. In normal operation, the springs 121 cause the plunger 48 to be in the "down" position. A vessel can be inserted by the user grabbing a plunger tab 127, which is a metal finger extending from plunger 48, and physically lifting up the tab and thus the plunger 48; inserting the vessel; and then letting the plunger 48 sit back down on the vessel. Thus the user has physically engaged the plunger 48 to the extraction vessel. Then the forcing mechanism 52 powers on and applies the force to seal the plunger 48 to the vessel.

Again referring to FIG. 1, the pumping mechanism 12 preferably includes a pump 34 and a first valve 36 which directs solvent from the pump 34 to the extraction mechanism 14 when the first valve 36 is in a first state and directs solvent from the extraction mechanism 14 to the atmosphere when the first valve 36 is in a second state. Additionally, the extraction mechanism 14 preferably also includes a second valve 38 connected to the first valve 36 to receive solvent from the first valve 36 when the first valve 36 is in the first state. The second valve 38 directs solvent to the first extraction chamber 26 when the second valve 38 is in a first state and directs solvent to the second extraction chamber 28 when the second valve 38 is in a second state.

In the operation of the preferred embodiment, a first sample 16 to be analyzed is placed into a first extraction vessel 30. Also, a second sample 18 to be analyzed is placed into a second extraction vessel 32. The first extraction vessel 30 and the second extraction vessel 32 are each sealed. See U.S. patent application Ser. No. 07/962,463, incorporated by reference. The first extraction vessel 30 is then inserted into the first extraction chamber 26. By the first extraction vessel 30 being inserted into the clip of the first extraction chamber 26, the clip holds the first extraction vessel 30 in the first extraction chamber 26 in a proper orientation for subsequent extraction of the analyte in the first sample. Similarly, the second extraction vessel 32 is inserted into a clip in the second extraction chamber 28. The clip holds the second extraction vessel 32 in a proper position for subsequent extraction of the analyte in the second sample 18.

After the first extraction vessel 30 and second extraction vessel 32 are properly positioned in the first extraction chamber 26 and second extraction chamber 28, the apparatus 10 for gathering analyte is activated by the user pressing the power ON button, to provide power to the system and then the user pressuring the START button.

When the apparatus 10 is activated, a plunger 48 of the first plunger assembly 44 and a plunger 48 of a second plunger assembly 46 move downward and penetrate into the first extraction vessel 30 and second extraction vessel 32, respectively. The penetration of the plunger 48 into a respective vessel, provides for a continuous channel through which analyte in the sample can be extracted and to seal the end of the vessel for high pressure operation.

Figure 12:
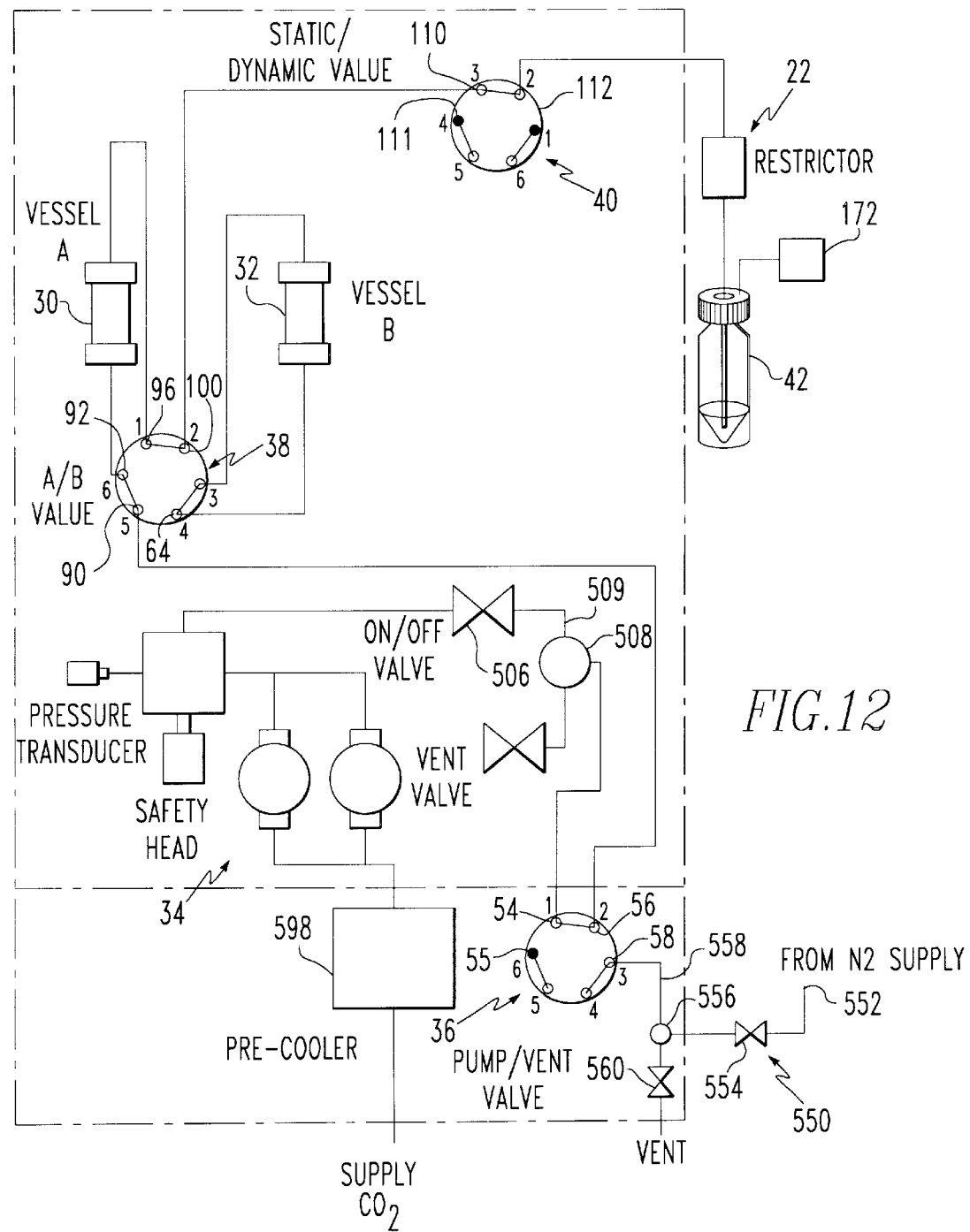
FIG. 12 is a schematic representation of an apparatus for determination of analyte concentration of the present invention.

Referring to FIG. 1, and the plumbing diagram shown in FIG. 12, when extraction begins in the apparatus 10, the pump 34 of the pump mechanism 12 pumps $CO_2$ at a supercritical pressure in excess of 100 atmospheres (atm) up to as high as 680 atm and pressures even to 1,000 atm, to the first valve 36. The first valve 36 receives the supercritical $CO_2$ through a first inlet 54. Pump 34 can use $CO_2$ source gas that has a helium head space applied to the head space of the $CO_2$ tank or Pump 34 can use cheaper grades of $CO_2$, such as food grade or industrial grade as the solvent gas. Sometimes it is difficult to get a helium headspace put on these cheaper grades of $CO_2$ gas, thus a precooler for pump 34 exists.

Figure 22:
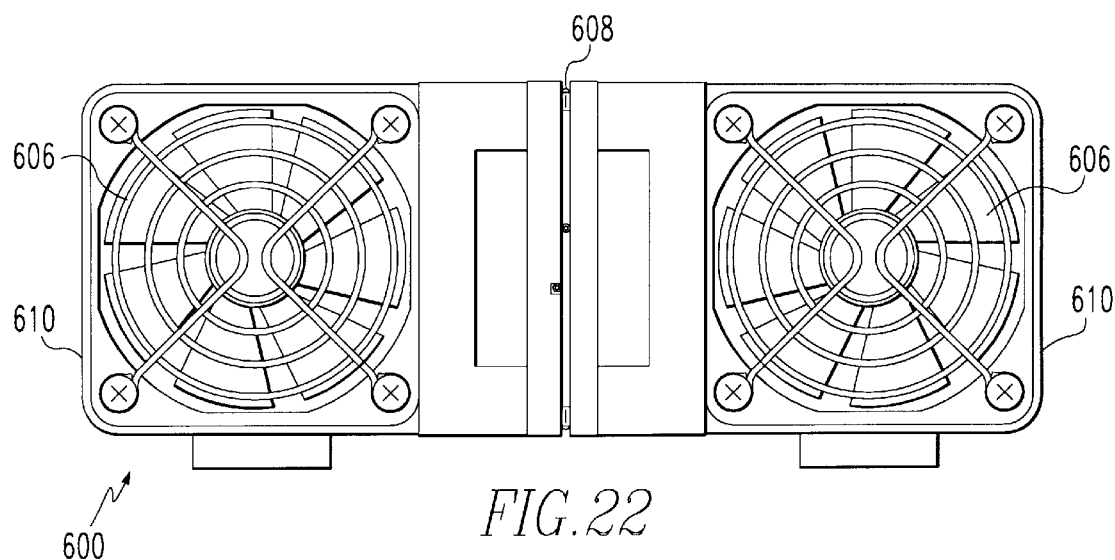
FIG. 22 is a schematic representation of cooling system.
Figure 24:
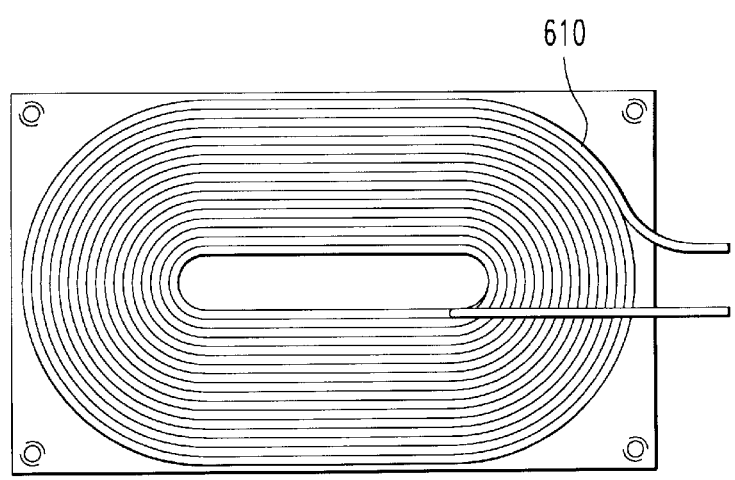
FIG. 24 is a schematic representation of the coil of the cooling mechanism.
Figure 23:
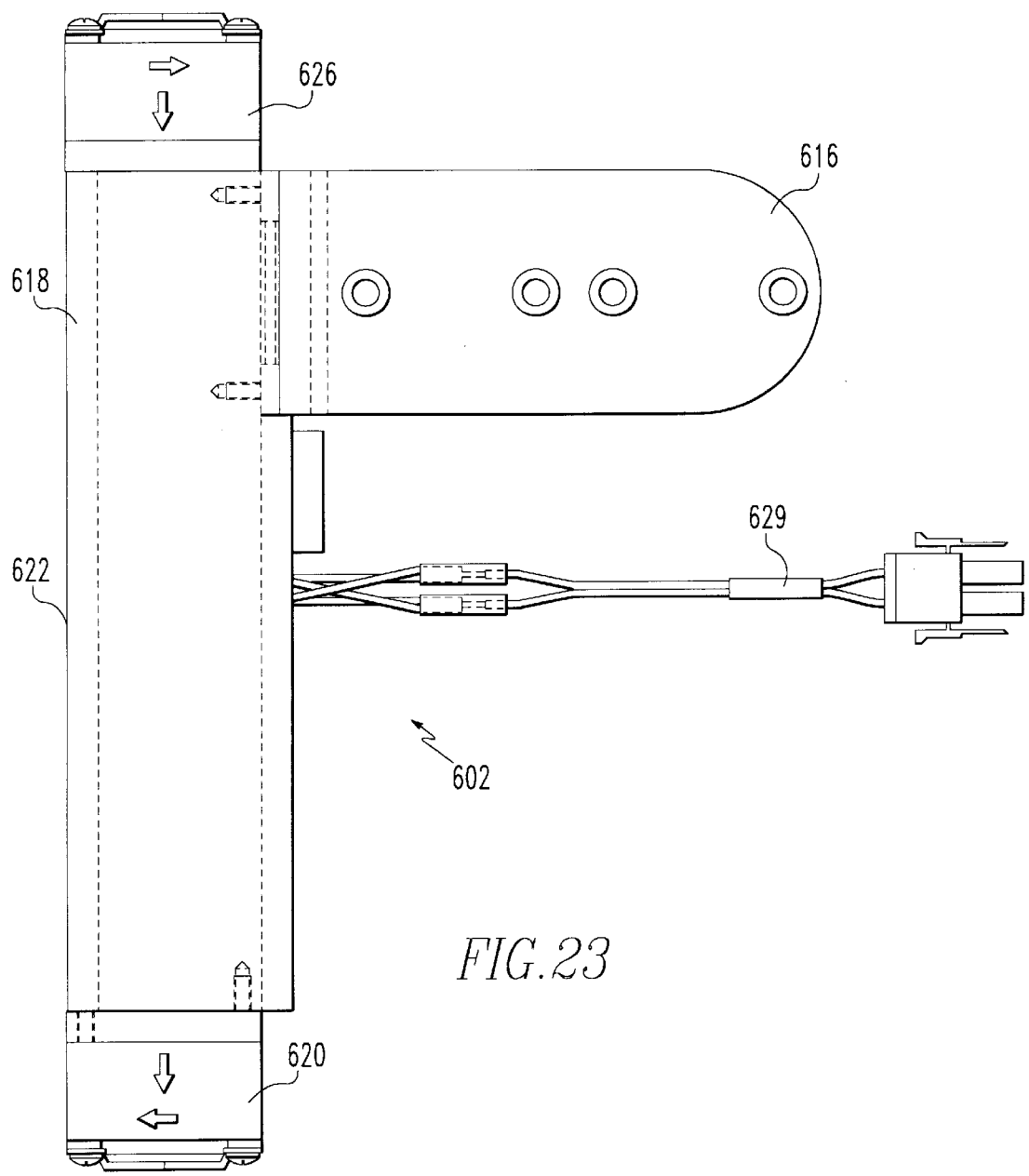
FIG. 23 is a schematic representation of the cooling mechanism.

Referring to FIGS. 1, 12, 22, 23 and 24, the precooler system 598 consists of two major parts, the super cooler assembly 600 (shown in FIG. 22) and pump head cooler assembly 602 (shown in FIG. 23). Both of these devices are in thermal contact with the $CO_2$ from a $CO_2$ source tank to the Pump 34. Referring to FIG. 22, the supercooler assembly consists of two thermo electric coolers 606, such as Supercool Model DA-020-12-022. These two thermo electric coolers have a cold side 608, which is in thermal contact with the $CO_2$ stream and a hot side 610, which contains a fan which expels the heat which builds up. The cold side 608 is in thermal contact with a tube coil 610 (as shown in FIG. 24). The $CO_2$ stream from the $CO_2$ source tank flows through coil tube 610, which in thermal contact with the cold side 608 of two thermo electric chillers. The temperature of the $CO_2$ fluid decreases, typically to a value of −5° C. to −10° C., as it flows through the tube coil 610. The reason for two thermo electric chillers is to add more cooling to the $CO_2$ gas. Alternatively, the amount of cooling needed could be obtained with one larger thermo electric chiller.

After the $CO_2$ gas passes through the tube coil 610, it flows onto and into pump 34. The pump heads of pump 34 have pump head cooler assembly 602 mounted on it as shown in FIG. 1. FIG. 23 shows a detailed view of pump head cooler assembly 602. Pump head cooler assembly 602 consists of a copper bracket 616 connected to a heat sink 618. Two fans 620 are mounted to each end of heat sink 618 and insulation 622 is attached to the outside of heat sink 618. Power is supplied to the fans 620 by cable 624 which is in turn hooked to a power supply. The purpose of pump head cooler assembly 602 is to add additional cooling to the heads of pump 34, so that the heads do not heat up due to either environmental heat or heat generated due to compression of $CO_2$ in pump 34.

When the first valve 36 is in a first state, the solvent flows through the first valve 36 and out it through a first outlet 56 which is connected with the second valve 38. If the first valve 36 is in a second state, then the pump 34 is connected to a plug 55, which effectively shuts off the flow from pump 34. In the second state of valve 36, outlet 56 is then connected to outlet 58, which allows for the automatic depressurization of the first extraction chamber 26 or the second extraction chamber 28, depending upon the state of valve 38, which is programmed by the user.

The plunger 48 in the first plunger assembly 44 and second plunger assembly 46 move under the action of pressure being supplied by a hydraulic system 135. The hydraulic system 135 is engaged based upon the system program supplied by control microprocessor 252 and computer 64. At the start of the extraction process, plunger assemblies 44 and 46 are programmed to move down to engage and seal extraction vessels 30 and 32. The hydraulic system pumps hydraulic fluid up to a specific pressure value as set by a pressure switch 137. This pressure set point is 1000 to 1200 pounds of force. This is the pressure needed to have the plunger assemblies 44 and 46 seal the respective extraction vessels 30 and 32, so that the vessels do not leak solvent to atmosphere.

Figure 3A:
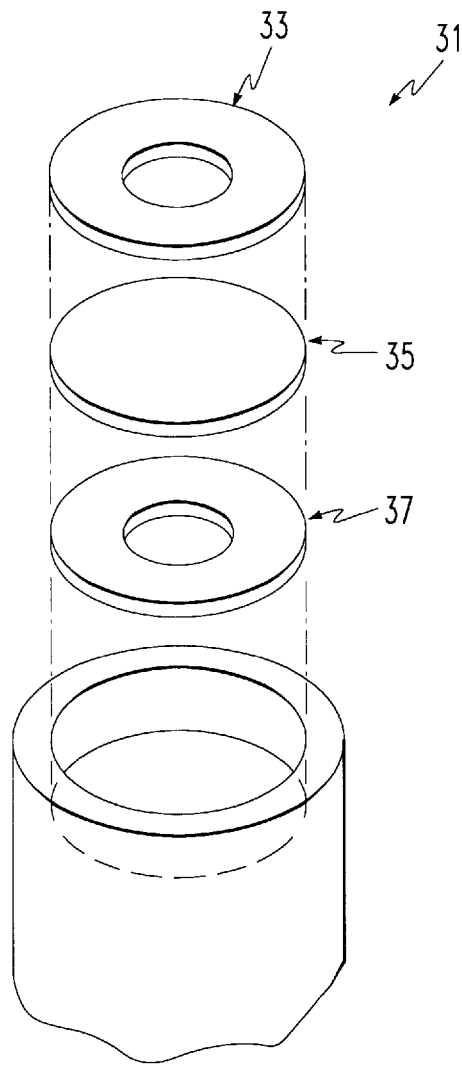
FIG. 3 is a schematic representation of a one-time use seal.
Figure 3B:
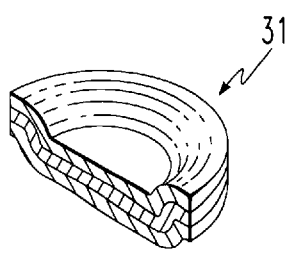

If it is so desired, seals that are used only one time, as shown in FIG. 3, can be combined with the vessel during the extraction process. In this case, a one-time use seal 31 is formed from a top disk 33, a middle disk 35 and a bottom disk 37. Each layer is placed atop the vessel with the bottom disk 37 placed first, the middle disk 35 placed on top of the bottom disk 37 and the top disk 33 placed on top of the middle disk 35. The top disk 33 can be made of acetal, such as the product Delrin® by DuPont. The middle disk 35 can be of filter paper and the bottom disk 37 can be of acetal also. When the extraction occurs, the holes in the center of the top and bottom disk allow solvent to pass through the middle disk 35 of filter paper. The seal 31 adapts to the inner walls of the vessel and when they are compressed by the plunger 48. When the vessel is removed from the extraction chamber 26, the seal 31 is simply lifted out of the vessel and thrown away. The top disk 33 of acetal can be between 0.2 and 0.3 inches thick, the middle disk 35 of filter paper can be 0.1 inches thick and the bottom disk 37 of acetal can be 0.02 to 0.03 inches thick.

Figure 13:
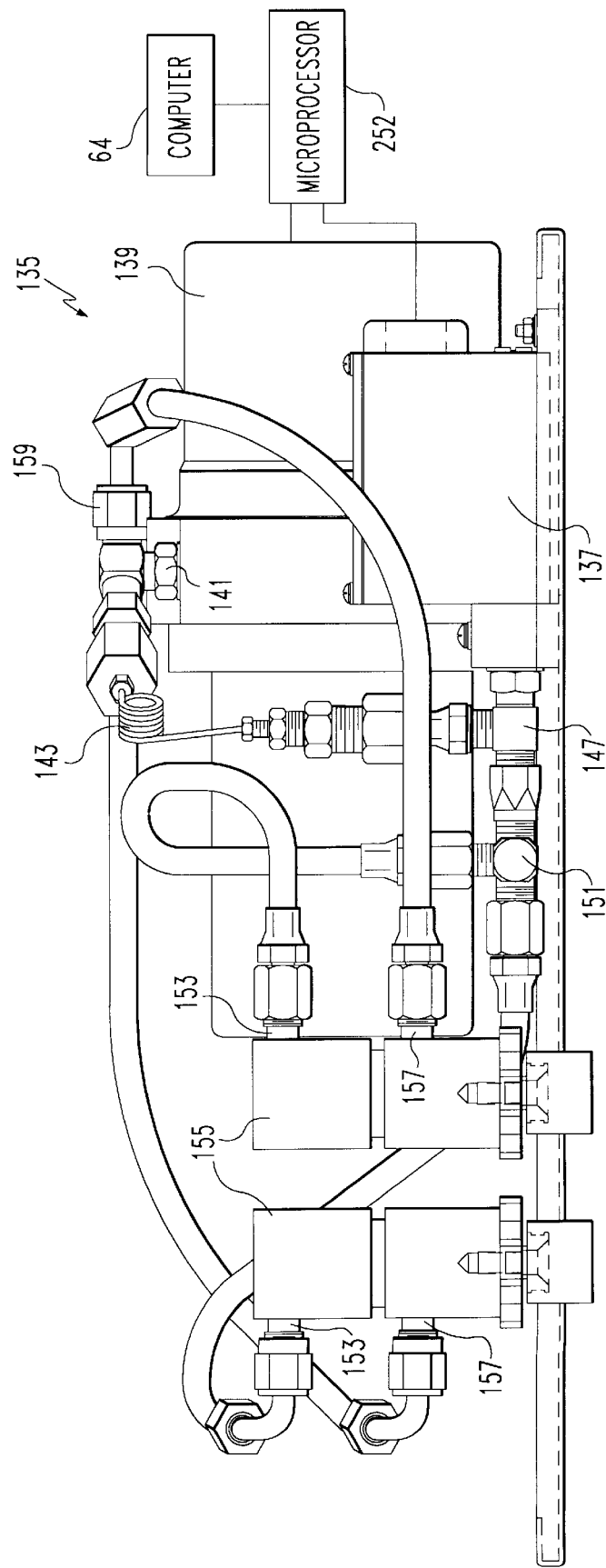
FIG. 13 is a schematic representation of a forcing mechanism of the present invention.

Referring to FIG. 13, which shows hydraulic system 135. The force applied to plunger 48 is created through the hydraulic system 135. Hydraulic pump 139, pumps hydraulic fluid out the outlet of the pump 141, through a coiled tube 143, and to a tee 147. One port of tee 147 is connected to a pressure switch 137. Pressure switch 137 is set through calibration of the switch to a pre-set value of 1000 to 1200 pounds of force. The other end of tee 147 goes to a second tee 151, where the plumbing line splits and goes to the two inlets of the hydraulic cylinders 153. The hydraulic fluids flows through the hydraulic cylinders 155 to the outlets of the outlets of the hydraulic cylinders 157. From outlet 157, the hydraulic fluid flows back to a tee 159, where the two lines are joined and enter the inlet of the hydraulic pump. Thus a re-circulating and closed hydraulic system is formed. Each hydraulic cylinder 155 is connected to plunger 48, which, in turn, is connected to either plunger assembly 44 or plunger assembly 46.

In normal operation, the computer 64 and control microprocessor 252 tells the hydraulic pump 139 to pump. Pump 139 starts to pump and pumps until the pressure switch 137 reaches the 1000 to 1200 pound set point. The pressure switch then sends a signal to computer 64, which in turns off the hydraulic pump. The rate of movement of the plunger 48 is controlled by coiled tubing 143. In the preferred embodiment, coiled tube 143 has an internal diameters of 0.020 inches and a length of 15 inches. If this internal diameter is larger and/or the tube is a shorter length, the pressure drop through the coiled tube 143 is smaller and the rate of movement of the plunger 48 is faster. Conversely, if the internal diameter of coiled tube 143 is smaller and/or the tube is a longer length, the pressure drop through the coiled tube is greater and the rate of movement of plunger 48 is slower.

Referring again to FIG. 1 and FIG. 12, the second valve 38 receives the supercritical solvent from the first outlet 56 of the first valve 36 through a first inlet 90. The second valve 38 receives the supercritical $CO_2$ at the first inlet 90 when the first valve is in the first state. The supercritical solvent that is received by the second valve 38 is directed to the first extraction chamber 26 through the first outlet 92 when the second valve 38 is in a first state. The second valve 38 directs the supercritical $CO_2$ to the second extraction chamber 28 through the second outlet 64 when the second valve 38 is in a second state.

When the second valve 38 is in the first state, the supercritical $CO_2$ passes through the first outlet 92 to the first extraction chamber 26, and into the first extraction vessel 30 that is held in the first extraction chamber 26 via a first base 93 upon which the first extraction vessel 30 is seated. The first extraction vessel 30 is seated onto the first base 93 when the plunger 48 penetrates into the first extraction vessel 30 under the action of the forcing mechanism 52 providing pressure to the plunger 48.

It is the first base 93 against which the first extraction vessel 30 is pushed by the action of the plunger 48 pushing down on the first extraction vessel 30 and penetrating into it. In the first base 93 is a tube 65 which extends through the first base 93. The tube 65 in the first base 93 is connected to the first outlet 92 of the second valve 38 and provides the supercritical $CO_2$ into the first extraction vessel 30 which is seated upon the first base 93.

The supercritical $CO_2$ flows through the first extraction vessel 30, extracting analyte from the first sample. It then enters a plunger tube 97 that extends through the plunger 48 which penetrates into the first extraction vessel 30 at an opposing side of the first extraction vessel 30 from the first base 93. The supercritical $CO_2$ having the analyte is passed through the plunger tube 97 in the plunger 48 of the first extraction chamber 26 and is provided back to the second valve 38 at its second inlet 96. When the second valve 38 is in the first state, the supercritical $CO_2$ with the analyte from the first sample 16 is guided by the second valve 38 out through a third outlet 100 of the second valve to the collection mechanism 20. During the time the second valve 38 is in the first state, no supercritical $CO_2$ can pass from the second extraction chamber 28 out of the second valve 38. The operation of the second valve in regard to the first outlet 92 and second inlet 96 is coordinated so flow can be established through the first extraction vessel 30 at a desired time.

In a similar manner to the extraction of analyte from the first sample 16 in the first extraction vessel 30, is the extraction of analyte from the second sample 18 in the second extraction vessel 32. However, in this case, the second valve 38 is in a second state and supercritical $CO_2$ then is allowed to pass through the second valve 38 via a second outlet 64 to the second base 99 of the second extraction chamber 28. The supercritical $CO_2$ flows through the tube 65 in the second base 99. The supercritical $CO_2$ then travels from the tube 65 in the second base 99 through the second extraction vessel 32 having the second analyte 18 therein and collects the analyte therefrom. The supercritical $CO_2$ with the analyte from the second sample 18 then passes through the plunger tube 97 of the plunger 48 of the second extraction chamber 28 to the second valve 38 where it is received at its third inlet 98. The third inlet 98 and the second outlet 64 are coordinated so they can be opened at the same time to allow a flow path for the supercritical $CO_2$ to exist through the second extraction vessel 32 to gather analyte from the second sample 18. When the second valve 38 is in the second state, no supercritical fluid can flow through the first extraction vessel 30.

The extraction process consists of two states: Static and Dynamic. The definition of these two states are 1) in a static state, the sample in the extraction vessel is exposed to solvent and that solvent is allowed to stay in the vessel (i.e there is no net flow of solvent through the vessel—the solvent is static), the static step increases overall extraction efficiency by allowing the solvent to better penetrate into the pore structure of the sample; 2) in a dynamic state, the solvent is continuously flowing through the sample and out the end of the extraction vessel, thus carrying out the analytes from the sample to the rest of the downstream system.

In this system, when valve 38 is in its first state and valve 40 is in its first state, the first sample 16 is in the dynamic state and the second sample 18 is in the static state. When valve 38 is in its second state and valve 40 is in its first state, then the first sample 16 is in the static state and the second sample 18 is in the dynamic state.

A typical method for a sample is shown in Table 2. The method in Table 2 can be interpreted as follows: The column named Line is the line of the method (many times this is called "stage" of the method); The columns for Valves 40, 38 and 36 are the program state for these valves. The Time column shows the amount of time that the program stage is programmed. The ATM column is the pressure set point of pump 12. The ° C. column is the temperature set point of thermal zone 47. The flowrate of the solvent is set on the top line of the method programming page.

Referring again to Table 2. First the system is equilibrated with valve 40 in the Static state (i.e. its second state), valve 38 is in the "A" position (i.e. its first state), there is no time set point, pump 12 is set to 550 atm, thermal zone 47 is set to 150° C., and valve 36 is programmed to the VT (for Vent) state (i.e. is second state). The system will now come to equilibrium at 550 atm and 150° C., taking whatever time it needs, but usually this is within 3 minutes. During this equil stage, sample 16 in extraction chamber 26 is being statically bathed in solvent. When the system actual pressure and temperature reaches its set points, the system will go onto stage 1 of the program.

In stage 1, valve 40 in the Dynamic state (i.e. its first state), valve 38 is in the "A" position (i.e. its first state), Time equals 5 minutes, pump 12 is set to 550 atm, thermal zone 47 is set to 150° C., and valve 36 is programmed to the PM (for Pump) state (i.e. is first state). In stage 1, the solvent flow is dynamic through sample 16 in extraction chamber 26 for 5 minutes at 550 atm, 150° C. and 4.0 ml/min flow. The analytes from sample 16 are flowing to collection mechanism 22. In stage 1, side A is in a dynamic extraction condition, while no $CO_2$ has reached side B (sample 18) at this time.

After the 5 minutes have occurred, the system automatically moves to stage 2. In stage 2, valve 40 in the Dynamic state (i.e. its first state), valve 38 is in the "B" position (i.e. its second state), Time equals 10 minutes, pump 12 is set to 550 atm, thermal zone 47 is set to 150° C., and valve 36 is programmed to the PM (for Pump) state (i.e. is first state). In stage 2, the solvent flow is dynamic through sample 18 in extraction chamber 28 for 10 minutes at 550 atm, 150° C. and 4.0 ml/min flow. The analytes from sample 18 are flowing to collection mechanism 22. In stage 2, sample 16 on side A is in a static extraction condition, while sample 18 on side B is in dynamic extraction condition.

Then, the system moves onto stage 3. In stage 3, Valve 40 is dynamic, valve 38 moves back to the "A" setting (its first state), and valve 36 remains in the PM state. This allows solvent into the A side vessel (sample 16 in extraction chamber 26) for 10 minutes at 550 atm, 150° C. and 4.0 ml/min flow. The analytes from sample 16 are flowing to collection mechanism 22. In stage 2, sample 16 on side A is in a dynamic extraction condition, while sample 18 on side B is in static extraction condition.

After 10 minutes, stage 4 starts, where sample 16 on side A is in a static extraction condition, while sample 18 on side B is in dynamic extraction condition for 5 minutes at 550 atm, 150° C. and 4.0 ml/min flow.

In stage 5, the valves are switched so that side A is static (i.e. Valve 40 is in its 2nd state), but valve 36 is to vent (i.e. its 2nd state). Thus no $CO_2$ is reaching Side A and Side A is open to atmosphere. At this time, Side A depressurizes to atmosphere. Side B is static at this time.

In stage 6, valve 38 switches so that Side B is depressurized to atmosphere.

Stages 7 and 8 represent a post-heating step where each side: A then B, is opened to vent for a period of 5 minutes each while heating of the sample is maintained at 150° C. This step is needed many times after an extraction to liberate remaining $CO_2$ from the matrix. If the analytical determination of the fat loss from the sample is made gravimetric weight loss (meaning weighting the extraction vessel before and after the extraction to determine weight loss), then this post-heating step is needed to remove any remaining $CO_2$ from the sample. If the post heating step is not performed, some additional weight due to the $CO_2$ will be recorded in the final result.

The alternating program allows throughput of the system (as measured in samples for hour) to be higher than in doing one sample at a time. This is due to the fact that a static extraction on one sample can be done in an overlapped fashion with the dynamic extraction of the second sample. Overall cutting down the time of extraction for the two samples taken in total.

The programming allows for great flexibility in the instrument operation. For example, only one sample can be run instead of two. The time, pressure, temperature and flowrate of the solvent can all be modified in any manner.

Referring to FIG. 12, by controlling the action of the second valve 38 and third valve 40 in the corresponding inlets and outlets, the extraction of the first sample 16 in the first extraction vessel 30 and the extraction of the second sample 18 through the second extraction vessel 32 can occur essentially simultaneously by alternating static and dynamic steps. For instance, the supercritical $CO_2$ can be allowed to enter the first extraction vessel 30 via the first port 92 of the second valve 38 but for a predetermined time, the second port 96 of the second valve 38 is effectively closed due to the third valve 40 being in the static state. This causes the supercritical $CO_2$ to fill the first extraction vessel 30 but not flow through it. While the supercritical $CO_2$ stays in the first extraction vessel 30, the supercritical $CO_2$ has more time to interact with the analyte, penetrate into the pore structure of the sample, and gather it (or extract it) from the first sample 16. Once the first extraction vessel 30 is charged with supercritical $CO_2$ and allowed to stay static for some period of time. The switching valve 38 is switched to allow the supercritical $CO_2$ to flow out of the port 64, thus allowing the second extraction vessel 32 to also be charged with supercritical $CO_2$ to extract the analyte from the second sample 18. In this case, also port 98 can be closed if valve 40 is in the static state, so that the supercritical $CO_2$ in the second extraction vessel 32 cannot flow out it. After the second extraction vessel 32 is charged, the valve can switch again so that port 98 is connected to port 64, port 96 connected to port 100, port 90 connected to port 92. At the same time, valve 40 switches to connect port 110 with 112. This creates a path of flow through the first extraction vessel 30 to remove the supercritical $CO_2$ with the analyte that had been in the first extraction vessel 30 and replace it with new supercritical $CO_2$ (i.e. a dynamic state). After a predetermined time, the valve switches again to connect port 90 to 64, port 98 to 100 and port 92 to 96, creating a path of flow through the second extraction vessel 32 for the supercritical $CO_2$ with analyte from the second sample 18 to flow out and be replaced with new supercritical $CO_2$ and to flow to the collection mechanism 22. This switching back and forth can occur as many times as desired for predetermined times as desired.

Supercritical $CO_2$ having analyte, whether it be received by the port 96 or the port 98 of the second valve 38, is then directed to the third valve 40 where it is received at a first inlet 110. When the third valve 40 is in a first state, the supercritical fluid that is received at the first inlet 110 is then allowed to pass to port 112 at third valve 40 to a restrictor 22. If the third valve is in a second state, then any supercritical $CO_2$ that is received at the first inlet 110 is stopped from passing through the third valve 40 by a plug in port 111.

Figure 2:
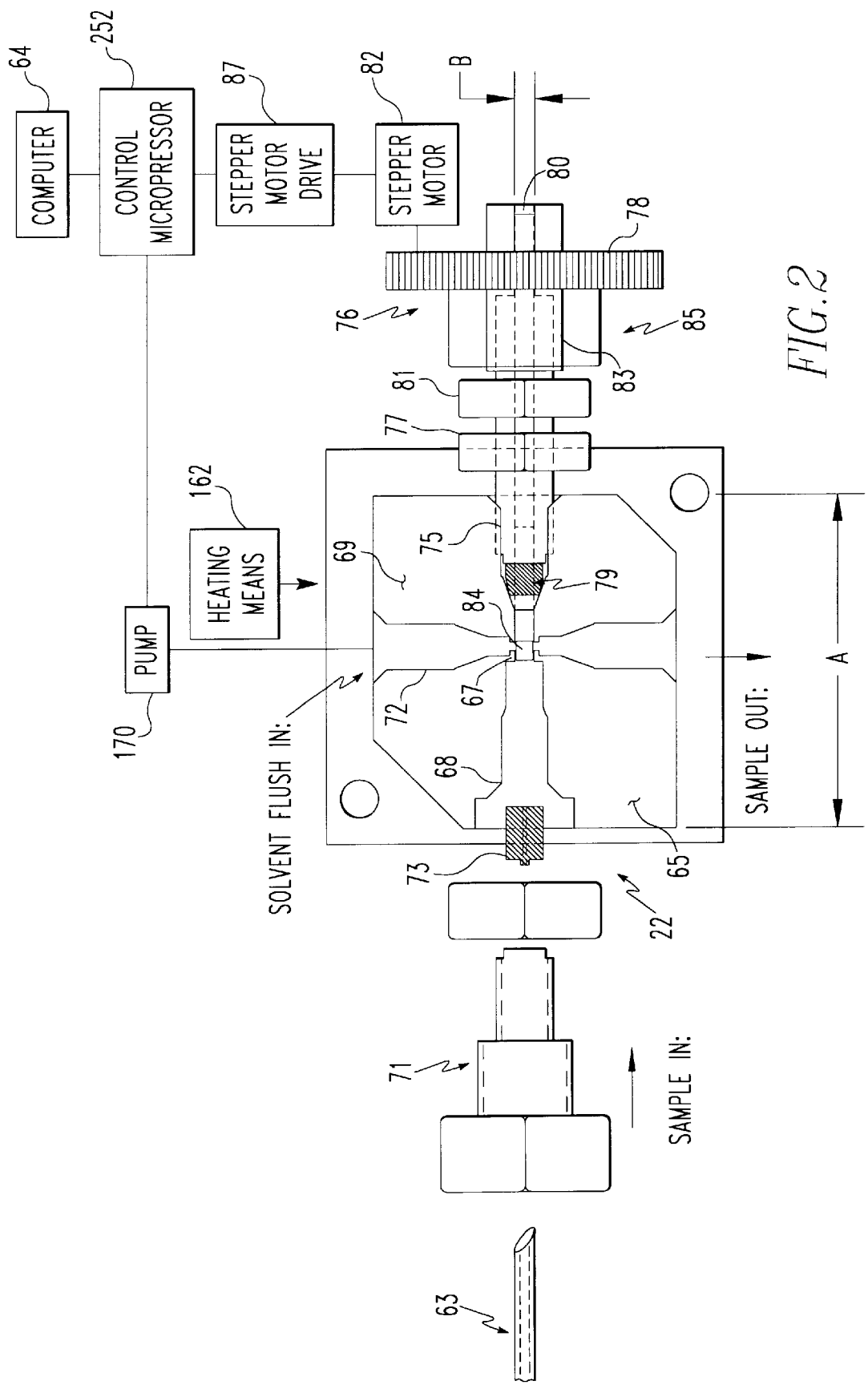
FIG. 2 is a schematic representation of a variable restrictor with the needle extended.

There is then a need to reduce the pressure of the supercritical $CO_2$ after it exits the third valve 40 from its high pressure (up to 680 atm or even 1,000 atm) down to atmospheric pressure so that the analyte can be effectively collected. Restrictor 22 does this automatically. Referring to FIG. 2, there is shown the restrictor 22. Preferably, the restrictor 22 is automatically controlled by the control microprocessor 252 and the computer 64. The restrictor 22 has a channel 65 which is preferably comprised of a first port 68 in fluidic communication with the first output 112 of the third valve 40, a second port 70 in fluidic communication with the collector 24 and a third port 72 which is plugged off with a mechanical plug. The third port 72 allows a means to add a liquid solvent wash to the restrictor mechanism for the purpose of cleaning the restrictor mechanism, if desired by the user. A portion 67 of the channel 65 has a variable inner diameter.

In a preferred embodiment of the restrictor 22, the portion 67 of the channel 65 with the variable inner diameter is a needle member 80 which adjustably projects into the first port 68 to restrict the flow of fluid with analyte therethrough. The first, second and third ports 68, 70 and 72 are threaded openings in a housing 69. The supercritical $CO_2$ with analyte is provided to the first port 68 through stainless steel tubing 63. Preferably, the tubing 63 has a $\frac{1}{16}$" OD and a 0.020" ID. The tubing is connected to an adapter 71, which is threaded into the first port 68 and sealed against seat member 73. Across from the first port 68 in the housing 69 is a fourth threaded port 75. An actuator mechanism 85 is threaded into the fourth port 75. The actuator mechanism 85 comprises needle member 80, a valve nut 81, which threads into the fourth port 75, and a first nut 77 having an opening which is threaded onto valve nut 81 to secure the needle member 80 into the fourth port 75. The valve nut 81 secures a ferrule 79 having an opening in the fourth port 75, to seal the fourth port 75. A needle member 80 projects through the opening of the first nut 77, valve nut 81 and the seal 79. A gear 78 is threaded onto a threaded extension 83. The gear is fixedly attached to the needle member 80 by a set screw in threaded extension 83. Threaded extension 83 is then threaded onto value nut 81. By turning the gear 78 on the threaded extension 83, the needle member 80 can be adjusted relative to the first port 68 and the seat member 73 contained within first port 68 to adjust the inner diameter of the channel 65 and create a depressurization area 84 where the high pressure $CO_2$ and analyte (if present) depressurize. The threading of the threaded extension 83 and the gear is extremely fine to allow for precise adjustment of the needle member 80. A motor 82 is used to turn the gear 78 on the threaded extension 83. The computer 64 controls the motor 82 based on desired flow of fluid through the control microprocessor 252, the stepper motor driver 87, and stepper motor 82.

Figure 14:
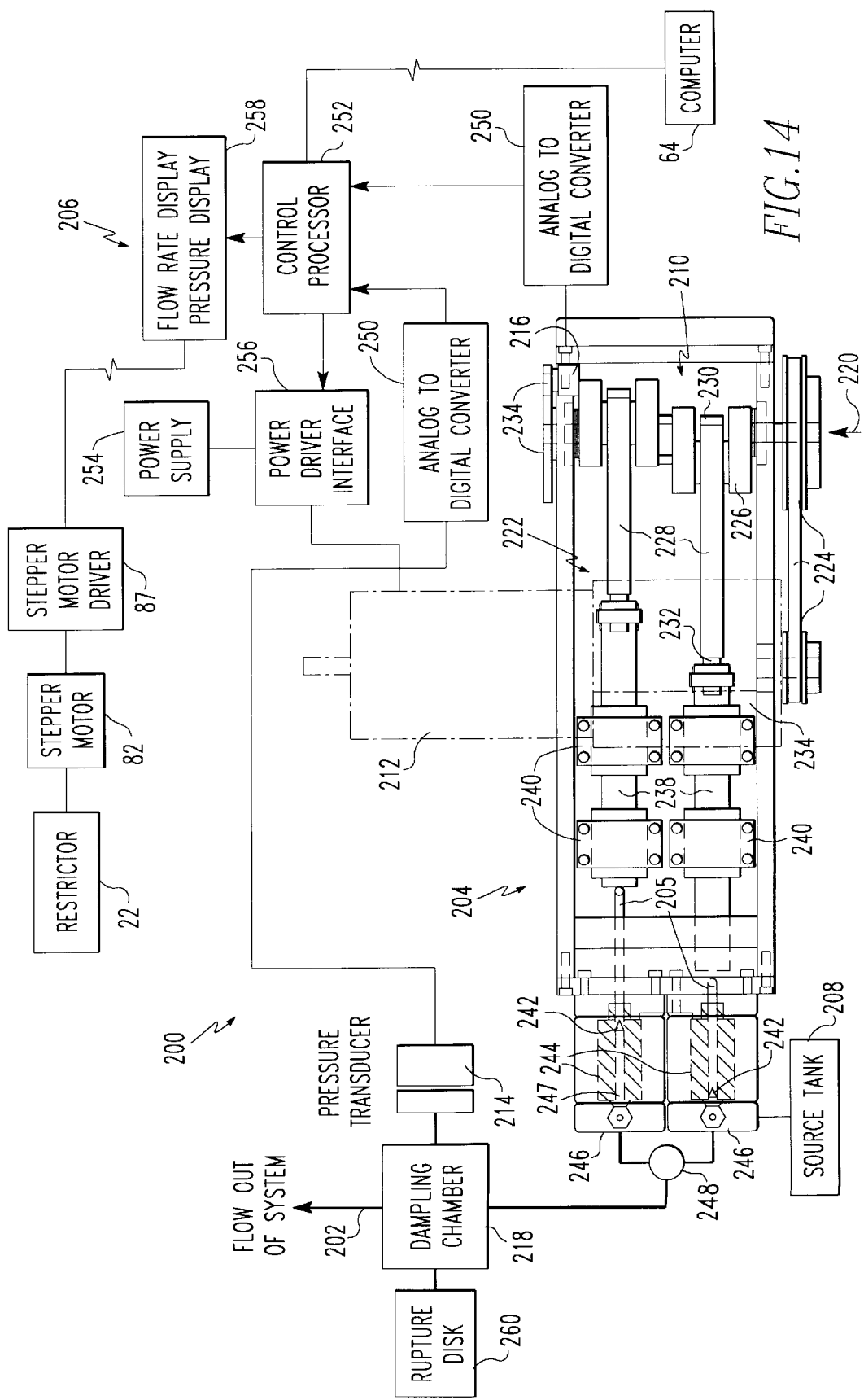
FIG. 14 is a schematic representation of an overhead view of the pumping mechanism.

Referring to FIG. 2 and FIG. 14, the control of restrictor 22 is accomplished by the user setting a desired flowrate in computer 64 which downloads to the control microprocessor 252 this desired flowrate. Control microprocessor 252 then calculates an actual flowrate of the pump (as described below) and compares the desired or set flowrate to the actual flowrate. Control microprocessor 252 then calculates if any corrective changes must occur in restrictor 22 by its control algorithms. If the actual flowrate does not match the set flowrate, then control microprocessor 252 sends to stepper motor driver 87 the number of motor pulses of change that should occur. The stepper motor driver 87 then controls stepper motor 82 to move that number of pulses. The motor moves the needle member 80 in restrictor 22 and a new flowrate is created. Then, the control microprocessor 252 calculates the new actual flowrate and the control cycle continues.

Figure 15:
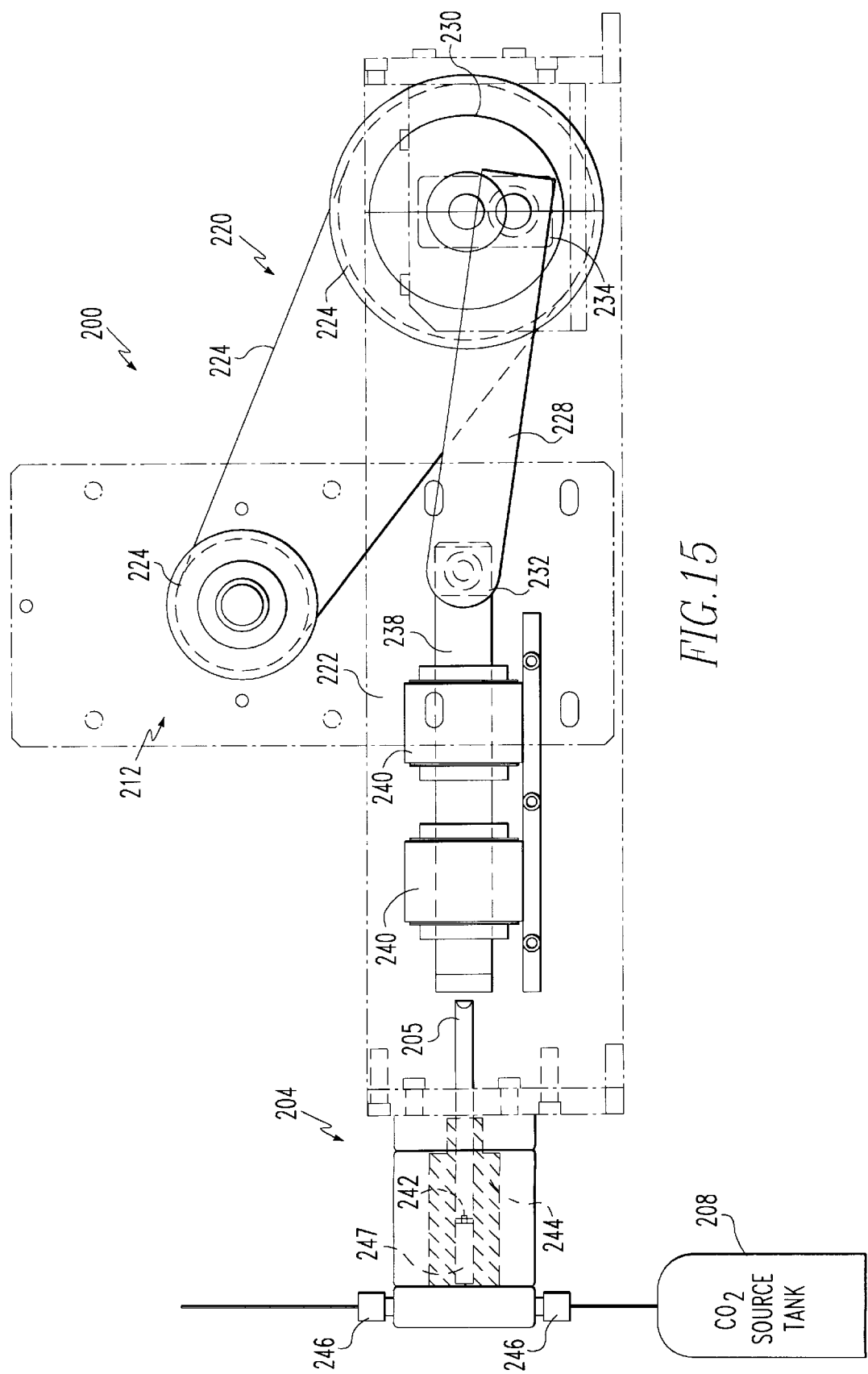
FIG. 15 is a schematic representation of a side view of the pumping mechanism.

The pumping system 200 comprises an output 202 from which supercritical fluid at a desired pressure and flowrate passes, as shown in FIGS. 14 and 15. The pumping system also comprises means 204 for providing supercritical fluid to the output 202. The providing means 204 is in fluidic communication with the output 202. The providing means has at least one variable speed piston 205 which pressurizes the fluid. The speed of the piston 205 at a given time corresponds to the pressure and flowrate of the fluid which passes from the output 202 at the given time. The pumping system 200 also comprises microprocessor control means 206 for controlling the providing means 204 such that the pressure and flowrate of the supercritical fluid provided by the output 202 is maintained at a desired pressure and flowrate. In a preferred embodiment, the providing means 204 includes a source tank 208, a pump assembly 210 having the piston 205 in fluidic communication with the source tank 208 and a motor 212 for driving the piston 205. The motor has a variable power input which is controlled by the microprocessor control means 206. The microprocessor control means 206 includes a pressure transducer 214 for measuring the pressure of the supercritical fluid at the output 202 and the microprocessor control means 206 comprises a piston position potentiometer 216. The output 202 comprises a damping chamber 218 which dampens the pulsations of the fluid passing from the pump.

Preferably, the pump assembly 210 comprises means 220 for providing rotary motion, and means 222 for converting the rotary motion into linear motion to drive the piston 205. Preferably, the rotary motion providing means 220 comprises a belt and pulley system 224 connected to the motor 212 and a crankshaft 226 connected to the belt and pulley system 224. Preferably, the means for converting the rotary motion into linear motion 222 comprises a crankarm 228 which is connected to the crankshaft 226 at a first end 230 and which is connected to pushrods 238 at a second end 232.

Rotary output from DC motor 212 is directly coupled into gear reducer 234. The gear reducer 234 decreases the speed and increases the torque of the rotary output from DC motor 212. The output of gear reducer 234 is coupled to the crankshaft 226 through the belt and pulley system 224. The belt and pulley system 224 provides additional speed reduction and torque increase. A gear system 236 translates the angular position of the crankshaft 226 to the piston position potentiometer 216. The gear system 234 preferably has an exact 2 to 1 gear ratio. Thus, each 180° rotation of the crankshaft 226 causes a 360° rotation of the piston position potentiometer 216. The crankarms 228 translate the rotary motion of the crankshaft 226 to a linear motion of push rods 238. Four stationary linear bearings 240 ensure that the motion of the push rods 238 remains linear despite the vertical forces translated from the crankshaft 226 through the crankarms 228. The push rods 238 in turn impart force to the piston 205. The crankshaft 226 is constructed so that the motions of the two piston 205 are exactly 180° out of phase. Therefore, one piston 205 will be moving forward while the other is moving backwards. Piston seals 242 make a gas and fluid tight seal with piston head liners 244. This prevents leaks of the fluid or gas being pumped. Paired inlet and outlet check valves 246 ensure that fluid may only be drawn from the source tank 208 and no fluid will be pumped back into the source tank 208.

Pumping action of the pumping system 200 occurs as a two phase process. In the first phase, the piston rod 205 is being withdrawn from the piston head liner 244. This causes a relative reduction in pressure within the pump head 247 and fluid is drawn into the pump head 247 through the inlet check valve 246. In the second phase, the piston 205 is pushed forward into the piston head liner 244. This causes the pressure to rise within the pump head 247. When the pressure in the pump head 247 exceeds the pressure in the damping chamber 218, the outlet check valve 246 opens and pressurized fluid flows from the pump head 247 into the damping chamber 218. A plumbing tee 248 allows delivery of fluid from whichever pump head 247 is currently in its second phase.

The damping chamber 218 is a reservoir of pressurized fluid used to reduce the pressure fluctuations seen by the output of the pumping system 200. A rupture disc 260 is provided in fluidic communication with the damping chamber 218 as a mechanical safety override for possible over pressurization of the pumping system 200. The pressure transducer 214 converts the pressure in the damping chamber 218 to a voltage. The output voltage of the pressure transducer 214 is converted to digital form by an analog to digital converter 250 and subsequently supplied to a control microprocessor 252. Similarly, the analog to digital converter 250 takes output from the piston position potentiometer 216 and converts it to digital form for the control microprocessor 252. There is a direct mathematical correlation between the crank shaft 226 angular position as read by the piston position potentiometer 216 and the linear position of the pistons 205. Thus, by applying the proper corrective formula the control microprocessor 252 can determine the linear position of either of the pistons 205. A regulated DC power supply 254 provides a source of energy that may be gated to the DC motor 212 via a power drive interface 256. The gating action of the power drive interface 256 is under direct and high speed control of the control microprocessor 252. Thus, the control microprocessor 252 can very rapidly apply and remove power from the DC motor 212. Finally, the control microprocessor 252 can write information for the user to read on a display panel 258. It should be noted that the pump system 200 does not require cooling when using a carbon dioxide source tank with helium lead space.

The control method of the pumping system 200 is described as follows. Assume some flowrate out of the pumping system 200 called the actual flowrate. Define a desired delivery pressure called the set pressure. Define the pressure read by the control microprocessor 252 via the pressure transducer 214 as the actual pressure. Define the flowrate displayed on the display panel 258 as the estimated flowrate. The control algorithm stored in the control microprocessor 252 must maintain the actual pressure as close as possible to the set pressure while displaying an estimated flowrate as close as possible to the actual flowrate.

In order to maintain a constant pressure within the damping chamber any fluid that exits from the damping chamber 218 must be replaced by an equal amount of fluid delivered from one of the pump heads. It must be noted that this is only true if the temperature of the compressed fluid remains constant throughout the system. The impact of temperature changes will be explored later, assume for the moment that the temperature remains constant.

As fluid flows out of the pumping system, the pressure within the damping chamber 218 begins to drop. This pressure drop is sensed by the pressure transducer 214 and the information is received by the control microprocessor 252. If an appropriate amount of power can be delivered to the DC motor 212, then whichever piston 205 is currently in compression will move forward and deliver enough fluid to restore the pressure in the damping chamber 218. If the difference between the set pressure and the actual pressure is used to determine the proper power to apply to the DC motor 212 in a continuous control loop then whichever piston 205 is moving forward will be pumping fluid at the same rate as the actual flowrate. In reality, the control loop is not continuous. The pressure is sampled and any noise is filtered out over a discrete time interval called the sample time. The power sent to the DC motor 212 remains constant during any given sample time. The power sent to the DC motor 212 is changed at the beginning of the next sample time based on the actual pressure recorded during the previous sample time. By keeping the sample time very short as compared with the mechanical reaction time of the pumping system 200, one can closely approximate the continuous control loop discussed earlier. Thus by using pressure feedback to control the power output to the DC motor 212 the forward motion of the piston 205 that is currently supplying supercritical fluid will match the actual flowrate. The rate of motion of either piston 205 can be accurately determined by reading the piston position potentiometer 216 and linearizing its output. The control microprocessor 252 can accurately determine time intervals using a quartz crystal as a time base. Therefore, an accurate estimated flowrate may be calculated by dividing the volume displaced by the pistons 205 that is supplying supercritical liquid by the time interval over which the fluid is being supplied.

Since control of the actual pressure is not perfect the forward motion of the piston rod 205 will not exactly match the actual flowrate. However, if the actual pressure remains close to the set pressure then the average motion of the pistons 205 will closely match the actual flowrate. Therefore, if an average piston position is taken over a suitably long time interval the estimated flowrate can be determined to a high degree of accuracy even in the presence of short term pressure errors. By using such an averaging technique the error on the estimated flowrate may be controlled at the expense of a slower overall response to changes in the actual flowrate.

Fundamental to the above control methodology is the assumption that the power output to the DC motor 212 can be changed. Variable power is delivered to the DC motor 212 as described in the following. A control interval time is chosen to coincide with the sample time described in the preceding section. This control interval time was further divided into 128 smaller time intervals called ticks. In order to set the power output to the DC motor 212 the power driver interface 256 is commanded to gate power from the DC power supply 254 to the DC motor for a fixed number of ticks during any control interval time. By changing the number of ticks that power is supplied during a control interval time the average amount of power to the DC motor 212 may be increased or decreased. In addition the power delivery is made smoother by distributing the ticks during which the power is supplied evenly amongst the ticks during which no power is supplied. This reduces the velocity changes that occur in the output of the DC motor 212 to a minimum thus resulting in better pressure control.

As stated earlier the assumption of constant temperature in the pumping system 200 is not totally accurate. Fluid is supplied into the piston head liner 244 at the temperature of the source tank 208. The fluid becomes heated during its compression from the pressure at which it arrived from the source tank 208 to the set pressure. The rise in temperature of the fluid within the piston head liner 244 causes its density to be reduced. The difference in density of the fluid in the warm piston head liner 244 to the density of the fluid in the cooler damping chamber 218 causes a difference in the actual flowrate as compared with the forward motion the pistons 205. This difference results in higher than expected estimated flowrates. By experimentally determining the magnitude of the flowrate error due to temperature effects an algorithm can be devised to compensate for these errors. The application of this temperature compensation can significantly increase the accuracy of the flowrate estimates. These flowrate estimates can then be used as the basis for the control of restrictor 22. The control of restrictor 22 is based upon a control algorithm that uses the estimated actual flowrate from the pump and compares it to the set flowrate programmed by the user. The supercritical fluid provided by the pumping system 200 is used to extract analyte from the sample within the extraction vessel 16.

If control microprocessor 252 calculates that actual flow is less than set point flow, then it will control needle member 80 to move away from the seat member 73 and thus open up the restrictor. If control microprocessor 252 calculates that actual flow is greater than set point flow, then it will control needle member 80 to move toward seat member 73 and thus close the restrictor. FIG. 2 shows the needle member 80 fully projecting into the first port 68. When the needle member 80 is retracted from the first port, for instance, the desorbing solvent from the third port 72 is allowed to freely flow to the second port 70, although it is not necessary to retract the needle member 80 from the first port to allow desorbing solvent to flow, since there is adequate clearance around the needle member 80 for the desorbing solvent to flow.

It is possible to also measure the flow of fluid through a supercritical fluid extraction system 10 by measuring the flowrate of gas that is expelled from the system past the restrictor 22. In order to collect the desired analyte, the supercritical fluid is allowed to expand to its normal volume at atmospheric pressure. Since there is a known density ratio between the supercritical fluid state and the expanded gas state the supercritical flowrate may be calculated from the expanded gas flowrate. By measuring the expanded gas flowrate with an expanded gas flow meter 172, as shown in FIG. 12, and performing the appropriate calculation the flowrate of the supercritical fluid exiting from the restrictor 22 can be determined.

Figure 16A:
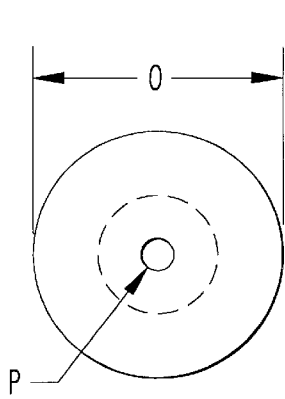
FIG. 16 is a schematic representation of a seat member of the restrictor.
Figure 16B:
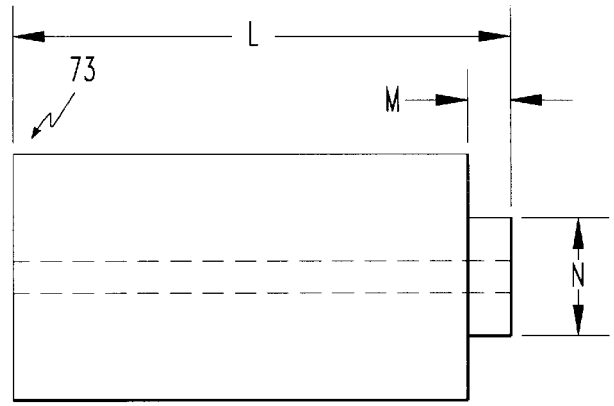

FIG. 16 shows a seat member 73. The following represents the dimensions as represented by reference characters L–P in FIG. 16.

M =0.28"
N =0.060"
O =0.140"
P =0.0156 ID
L =0.290"

It should be noted that the restrictor 22 has very small dimensions as compared to previous SFE restrictors. For instance, the total assembled length and width of the restrictor 22 is less than 2.5 inches and 1.5 inches, respectively. In this manner, reliable and precise control of supercritical fluid restrictor can be accomplished with a restrictor which is extremely small, and thus has extremely small dead volume. Small dead volume is important because the smaller the dead volume, the less likely that the restrictor will plug with analytes because the analytes do not have a volume to collect in or lodge in and thus start to form a plug. The small dead volume also reduces cross-contamination because analytes from a previous extraction do not have a place to collect and thus contaminate the extraction of analytes from a subsequent extraction. The restrictor 22 preferably has a minimum dead volume of 0.31 microliters, a maximum dead volume of 0.86 microliters and a nominal dead volume of 0.50 microliters.

Restrictor 22 also has the following additional advantages. The variable restrictor has the ability to accurately control carbon dioxide flows preferably in the 0.3 to 20.0 ml/min. range due to its very small dimensions and the control algorithms previously discussed.

Restrictor 22 has the ability to keep the depressurized carbon dioxide from freezing in the outlet of the valve, due to the heating means 162 (see FIG. 2). The heating means 162 consists of a cartridge heater and an RTD. The cartridge heater is connected to a power source controlled by control microprocessor 252 and the RTD is connected through a relay also to control microprocessor 252. Control microprocessor 252 then reads the RTD and compares that actual reading to the set temperature, as set by the user on computer 64, and then controls the power supply and thus the cartridge heater so that heating means 162 reaches the set temperature. Heating means 162 heats housing 69 which in turn heats the fluid flow entering first port 68, such that the expanded gas exiting second port 70 does not freeze. Supercritical fluid carbon dioxide upon depressurization, expands rapidly and cools due to Joule-Thompson effects. Carbon dioxide freezes into a solid at temperatures less than minus 65° C. Heating means 162, which is controlled at temperatures typically between 50° C. to 100° C. is powerful enough to overcome the Joule-Thompson effect so that the fluid exiting second port 70 is in the temperature range of –50° C. to +30° C. and preferably 25° C.

Restrictor 22 also has advantages over previous restrictor devices in that it has a ferrule 79 to seal the needle member 80 into the fourth port 75. The ferrule 79 has smaller dead volume than spring loaded seal with a larger dead volume. The smaller dead volume has advantages as described previously. Restrictor 22 also is constructed of stainless steel with poly-ether-ether-ketone (PEEK) seals. This has advantages over previous designs such as disclosed in U.S. patent application Ser. No. 07/848,424, incorporated by reference, because of increased durability, lack of fatigue of PEEK tubing parts, and smaller mechanical forces to automate which require smaller motors and less expensive cost.

Restrictor 22 also provides more precise control due to the PEEK seat member 73. Since the seat is made of PEEK instead of the more typical stainless steel or specialty steel, the seat member 73 is more pliable. Thus, seat member 73 flexes under the load of needle member 80 and this allows for more precise control of the restrictor. Thus, restrictor 22 can more precisely obtain a set flowrate than previous restrictors. Even though the seat member 73 is pliable, it cannot be too pliable or the seat will yield and thus fail after some time. This seat member 73 made from PEEK is durable enough to last for an extended amount of time, yet pliable enough to allow more precise control. Alternatively, carbon-reinforced PEEK and other types of PEEK composite materials make good restrictor seats.

Restrictor 22 also employs stepper motor 82 to drive the needle member 80. The use of a stepper motor 82 allows for more precise control because the turning of the stepper motor can be precisely controlled via stepper motor driver 87 and control microprocessor 252.

Another advantage of restrictor 22 is the ability to totally flush the restrictor with a flush liquid which is the same liquid used as the desorbing solvent dispensed by pump 170, as shown in FIG. 2. Since the third port 72 exists and is plumbed to pump 170, pump 170 can dispense a liquid solvent such as methanol, methylene chloride, or other common liquid solvent that flows into the third port 72 and exits from the second port 70. This desorbing or flush liquid then can wash the needle member 80, housing 69 and seat member 73 to clean out any residual analytes that could have deposited on the inner surfaces of restrictor 22. Since the pump 170 is used for this restrictor flush and is controlled from computer 64, the entire flushing of restrictor 22 can be automated and pre-set by the user.

Yet another advantage of restrictor 22 is that it is flow controlled versus pressure controlled. The parameters of pressure, temperature and fluid flowrate all effect the extraction efficiency of SFE. Pressure and temperature have the largest effects while flow the smallest effect. In the prior art, the systems typically operate with either a flow controlled pump combined with a variable pressure controlled restrictor or a pressure controlled pump with a fixed, nonvariable restrictor to control flow. System 10 incorporating restrictor 22, combines the pressure controlled pump with a variable flow controlled restrictor. This allows the fastest (in time) control response to be at the fluid providing means 12 which controls pressure, a more critical parameter to the extraction, and the slower (in time) control response for flow on the restrictor where it is less critical. Alternatively, restrictor 22 could be operated with a pump in flow control mode and restrictor 22 in a pressure control mode.

Another advantage of restrictor 22 is its ability to allow water to pass through the restrictor without plugging. The restrictors used in the prior art are very susceptible to plugging when water passes through the restrictor. Many types of environmental samples have a water content. Although there are methods to absorb the water during the extraction step, it is much easier to just let the water become both solubilized and entrained in the supercritical fluid flow exiting the extraction vessel and then to carry that water through the restrictor and into the collection means.

The problem in the prior art in doing this is that the water typically plugs the restrictor. Restrictor 22 does not have this problem. When water goes through the restrictor 22, the water causes the flow to slow down, the restrictor control system detects this and opens up the restrictor 22 to flow by moving the needle member 80 away from seat member 73. In this manner, restrictor 22 has been tested by filling an extraction vessel with 5 milliliters of water, pressurizing the vessel with 500 atm of carbon dioxide and then opening up a valve to allow the water to flow through restrictor 22. The plug of pure water being pushed through restrictor 22 by the $CO_2$ does not plug the restrictor 22.

Another advantage of restrictor 22 is its ability to allow high modifier concentrations to pass through the restrictor without plugging. The restrictors used in the prior art, especially restrictors made of fused silica, are very susceptible to plugging when any high level of modifier (greater than 10%) passes through the restrictor. Restrictor 22 operates smoothly according to the control algorithm when using modifier concentrations as great as 80%.

Another advantage of restrictor 22 is that there is low pressure on ferrule 79 and in ports 72, 75 and 70 since the depressurization zone 84 occurs upstream of these three ports. This allows easier securing (and thus leak tightness) of ferrule 79 since it does not have to hold high pressures. The same is true of any plumbing or mechanisms plumbed into ports 72 and 70.

Figure 17:
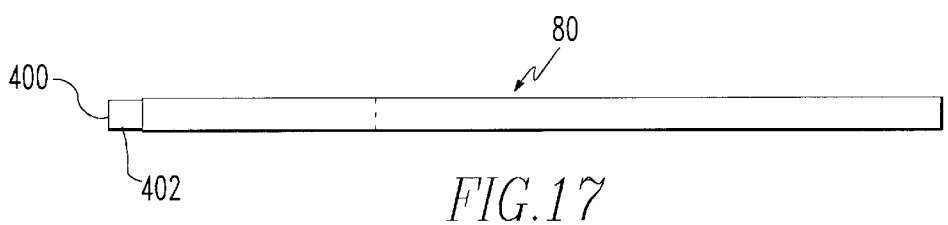
FIG. 17 is a schematic representation of a needle member of the restrictor.

The needle member 80 has a flat end with a step down in the end of it, as shown in FIG. 17. The flat end 400 of the restrictor 402 allows for improved reliability as the end of the restrictor can actually touch the restrictor seat 73 repeatedly without any side effects. When the older pointed needle design came in contact with the seat it tended to open up the hole through the seat 73, degrading performance over time. The step down on the end of the needle 402 allows for desorbing solvent flow to easily flow around the needle even if the needle is in contact with the seat. This allows the restrictor to be cleaned up easily with solvent if the inside surfaces become contaminated with analytes.

Other improvements include materials of construction. It is desired that needle member 80 be made of a material that has a low coefficient of thermal expansion, so the needle expands and contracts as little as possible during the large temperature shifts that occur in normal operation as $CO_2$ expands and thus cools down the restrictor and then $CO_2$ flow is shut off and the heating means 162 heats up the restrictor member 80. Thus, the needle member is made of tungsten, which has a low coefficient of thermal expansion.

Alternatively, various forms of stainless steel, quartz, or other materials with low thermal expansion coefficients can be used as a needle member. In the same manner, there are material issues with the restrictor seat 73. The current embodiment of restrictor seat 73 is that it is made of carbon filled poly-ether-ether-ketone polymer, which is both durable and has a lower coefficient of thermal expansion. Other materials that are both durable and have a low value for thermal expansion can be used for the restrictor seat 73. These material include stainless steel, tungsten, or quartz.

Figure 18:
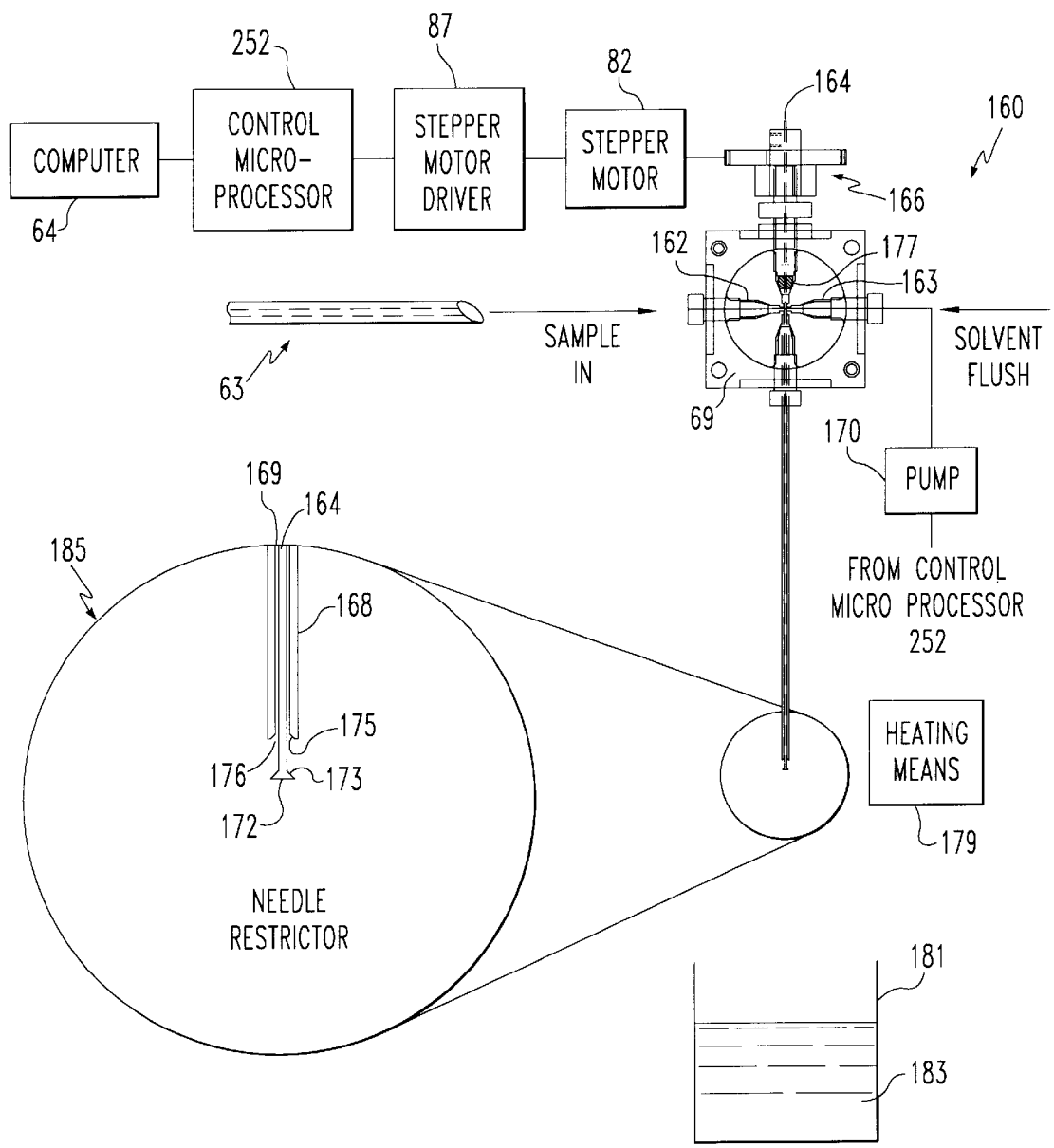
FIG. 18 is a schematic representation of an alternative embodiment of a restrictor.

As an alternative to restrictor 22, a new design of restrictor 160 can be used, as shown in FIG. 18. An inlet port 161, a port for the solvent wash 163 and a needle member 164 are all parts of restrictor 160. The needle member extends from the actuator mechanism 166 down an outlet tube 168. An annular area 169 exists between the outside of needle member 164 and the internal diameter of outlet tube 168. The needle member 164 is terminated with a needle end 172 which flares out from the stem of the needle member 164. Needle end 172 has a seating surface 173 which mates with a similar seating surface 175 on the outer tube 168. The mating of the seating surfaces 173 and 175 form the restriction area of restrictor 160 and the depressurization of the $CO_2$ occurs in this depressurization area 176.

In normal operation, flow from the extraction system 14 flows through tube 63 to the inlet port 161 and from there to the annular area 169. The flow flows down this annular area 169 through the length of the outlet tube 168 to the depressurization area 176, where the high pressure flow decompression occurs.

The actuator mechanism 166 is similar to the restrictor mechanism in FIG. 2 as it consists of parts 64, 252, 87, 82, 78, 83, 81 and 77. The differences in the actuator mechanism 166 versus that in FIG. 2 is that needle member 164 is much longer and shaped different than needle member 80; needle member 164 can also be of a smaller outside diameter (OD) than needle member 80. If needle member 164 is of smaller OD than needle member 80, then ferrule 177 must have a smaller internal diameter (ID) than the ID of ferrule 79. Most importantly, the difference between restrictor 160 and restrictor 22 is that in restrictor 160 the depressurization area 176 and seat area 173 and 175 are remote and much more physically separated from the actuator mechanism 166 than in restrictor 22 where the depressurization area 84 and seat 73 are much closer physically to the actuator mechanism 85.

In restrictor 160, the high pressure $CO_2$ with analyte enters in port 161 and thus exposes the needle member 164 and ferrule 177 to the high pressure. Thus, ferrule 177 has to seal against a high pressure since it is upstream of depressurization zone 176, whereas ferrule 79 of restrictor 22 only has to seal against low pressure since ferrule 79 is downstream of the depressurization zone 84. In the preferred embodiment, the outside diameter of needle member 164 is 0.011 to 0.020 inches and the length of needle member 164 is 0.5 inches to 12 inches.

Figure 21:
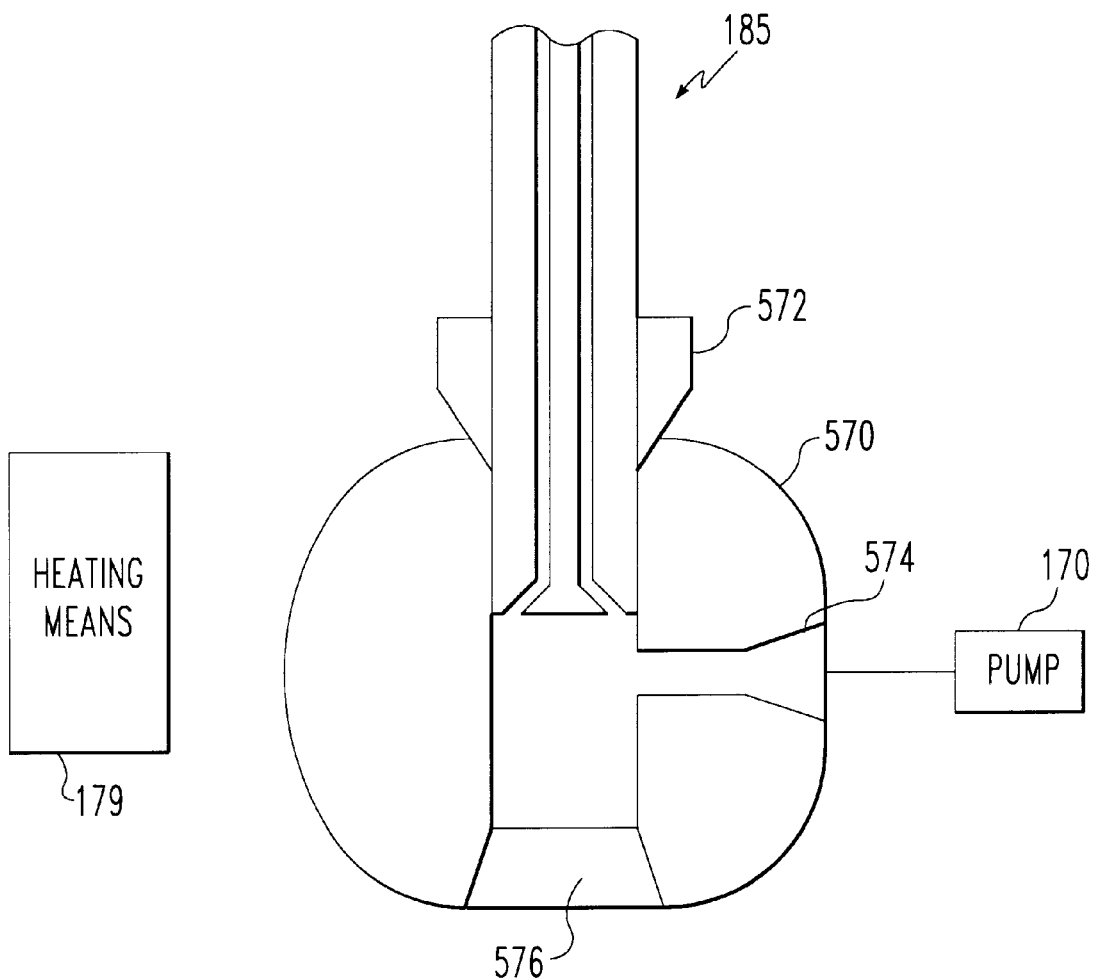
FIG. 21 is a schematic representation of a tee of the present invention.

There are three methods of solvent wash of restrictor 160. Referring to FIG. 18, in one method, when it is time for a solvent wash of the restrictor, the $CO_2$ from through tube 63 is shut off by doing a static dynamic valve upstream of the restrictor 160. This also prevents solvent wash from flowing out the first port. The solvent from pump 170 enters the inlet port for the solvent wash 163 and then flows down the annular area 169 through the length of the outlet tube 168 to the depressurization area 176. The solvent pump has a check valve which prevents solvent from the first port flowing to the solvent pump. In the second method, the restrictor end 185 is immersed in a solvent 183 contained in a vial 181. Thus, the solvent washes the surfaces 175, 173 and 172. A third method for restrictor washing is to plumb the restrictor end 185 into a tee such as shown in FIG. 21. Restrictor end 185 is fitted into a modified tee 570 and is secured into place with a ferrule 572. Pump 170 is plumbed into port 574. The outlet of the restrictor flow and the solvent wash flow then flows out port 576. Typical wash solvents in all these methods are common liquid solvents such as methanol, methylene chloride, acetone, hexane, etc. Referring to FIG. 18 and FIG. 2. In restrictor 22 heating means 162 heats housing 69 to keep the depressurized $CO_2$ from freezing the outlet port. In restrictor 160, the heat does not have to be supplied to block 69 but needs to be supplied to restrictor end 185 where the depressurization occurs. The plunger stem area does not have to be heated. The separation of actuator mechanism 166 and depressurization area 176 permits the depressurization area to be at any distance from the actuator. This physical separation of actuation and depressurization allows the restrictor end to have less physical mass to heat than in restrictor 22 and thus the heating means 179 which heats restrictor end 185 can heat the restrictor end more efficiently and with improved response versus the heating of restrictor 22. This improves flow or pressure control response to temperature imbalances due to the depressurization of the $CO_2$. The miniaturization of the needle member and the seat reduces further the energy requirement and improves thermal responsiveness as well as reducing areas that need to be cleaned.

In restrictor 160, the heating means 179 can use various methods of heating including 1) inductive heating, 2) conductive heating from a cartridge heater, 3) heating supplies by a solvent 183 in a vial 181, 4) convection from hot air, 5) microwave heating, 6) preheating the $CO_2$/analyte before depressurization, or any other type of heating device or mechanism.

The separation of actuator mechanism and the depressurization area also permits easier replacement of the seat, for cleaning or change of materials. It would be possible to provide different seat materials for different performance (higher temperature, higher flow). The preferred materials of construction of the needle member and the outer tube are stainless steel, carbon steel and other types of thermally conductive materials.

Figure 19:
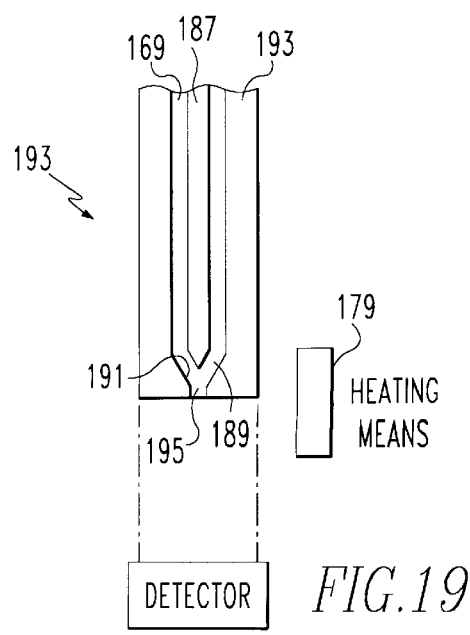
FIG. 19 is a schematic representation of another alternative embodiment of a restrictor of the present invention.

An alternative to restrictor end 185 is shown as restrictor end 193 in FIG. 19. In FIG. 19, the needle member 187 is pointed. Seating surfaces 189 exists at the end of needle member 187. A similar seating surface 191 exists on the internal diameter of the outer tube 193. The $CO_2$ and analyte flows down annular area 169 in the same fashion as in restrictor end 185. In restrictor end 193, the depressurization area is 195 and the seating surfaces are further inside the outer tube 193 than in restrictor end 185. The advantages of this design are that the restrictor side pulls out from the actuator side; there is no needle member extending from the lower end of the needle and thus it is somewhat more robust; and the outer tube 193 can be made to be sharp on the outside of the restrictor end 193, thus making the entire restrictor end 193 easier to pierce a septum.

The variable restrictors described here could be used in a number of applications in SFE and in supercritical fluid chromatography (SFC). The SFE applications include the depressurization of supercritical flow into an analyte trap, into a solvent or solvent trap, into a waste vial, or into the inlet port of a gas chromatograph, liquid chromatography or supercritical fluid chromatograph. The purpose of the use of the variable restrictors into the various types of chromatography is to perform on-line analyses where the SFE instrument is directly coupled to the analytical chromatograph. In a similar manner, the variable restrictor could be coupled to an infrared detection device (IR) or a mass spectrometer (MS). In SFC, the use of the variable restrictor to directly couple the outlet flow from a SFC chromatography column to a flame ionization detector (FID), nitrogen phosphorous detector (NPD), ultraviolet detector (UV) or mass spectrometer (MS) is also possible to provide the ability to control both the pressure and the flow rate of the supercritical fluid flowing through the chromatography column and into the detection device. In all these instances, where the restrictor is connected to the detector or column by the tubing extending around the restrictor end 193 to capture fluid as it leaves the restrictor end 193. See U.S. Pat. No. 5,372,716, incorporated by reference, for SFE coupled to an analytical chromatography system.

Again referring to FIG. 1, a collector tube 130 is connected to the second port 70 of the restrictor 22 and extends down into the vial 42. When the supercritical $CO_2$ passes through the restrictor 22, its pressure essentially goes to atmospheric pressure causing the analyte to solidify in the vial 42 where it is collected and the $CO_2$ escapes into the atmosphere or alternatively, it can be plumbed to a vent or exhaust hood system.

Figure 20:
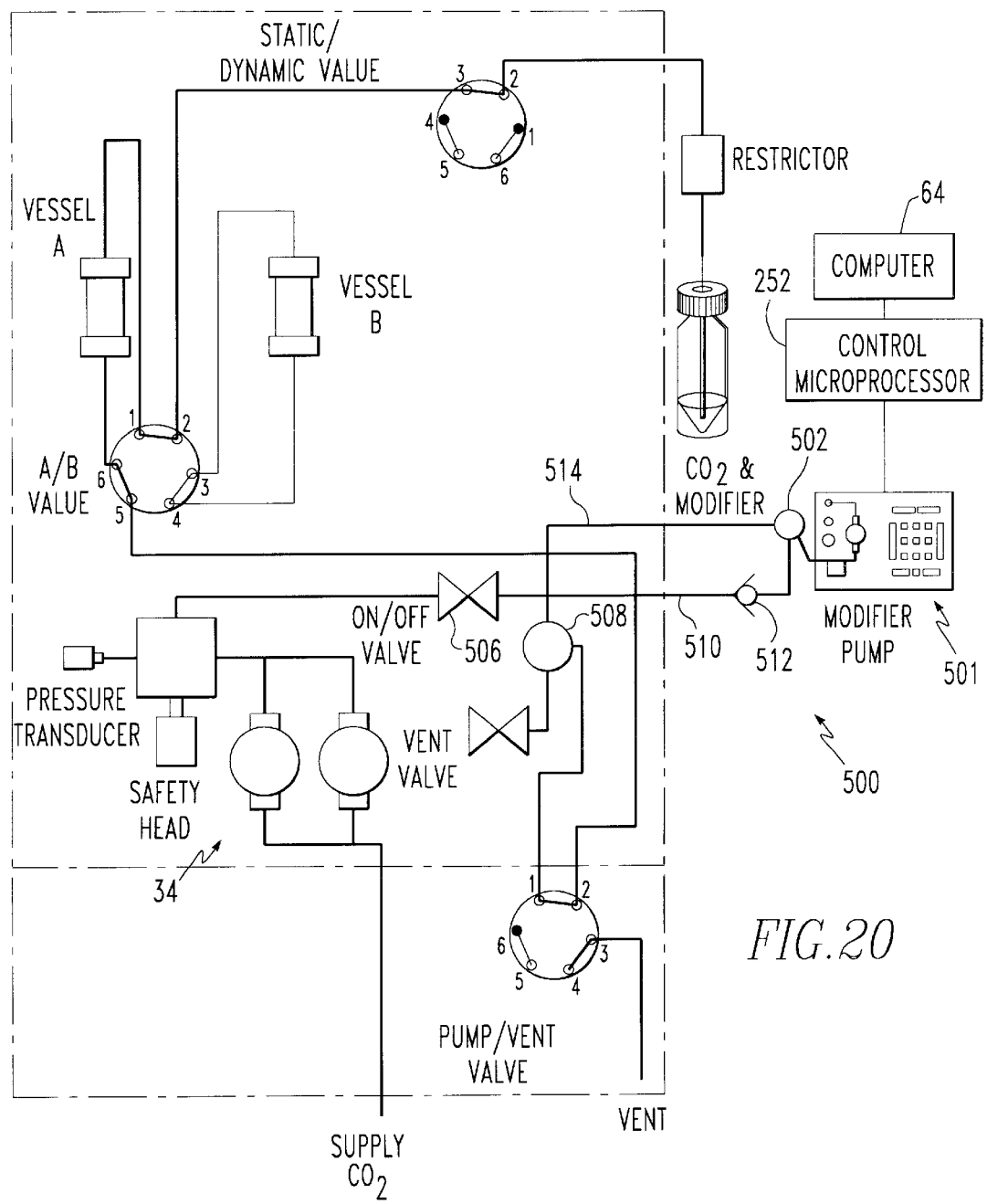
FIG. 20 is a schematic representation of an apparatus for determination of analyte concentration including a modifier pump.

As shown in FIG. 20, the SFE system 10 preferably also includes means 500 for providing a modifier to the supercritical fluid. The modifier providing means 500 is in fluidic communication with the supercritical fluid providing means 12, such as through a mixing tee 502. The modifiers are typically a liquid organic solvent such as methanol, methylene chloride, ethanol, propylene carbonate, acetone, tetrahydrofuran, fomic acid, etc. that are blended with the carbon dioxide in 1 to 80% by volume or mole percent to form a mixture that retains much of the diffusion characteristics of the pure carbon dioxide phase but which has a much higher polarity and thus is able to solubilize polar analytes and extract the polar analytes from the sample matrix. The modifier providing means 500 can include a plurality of modifier pumps for providing a plurality of different modifiers to the mixing tee 502. In this manner, a modifier mixture of the appropriate polarity can be added to the supercritical fluid to provide the specific polarity necessary during the extraction of each extraction vessel 30 and 32. Further, explanation on the use of modifiers can be found in S. H. Page, S. R. Sumpter, M. L. Lee, "Fluid Phase Equilibria in Supercritical Fluid Chromatography with $CO_2$-Based Mixed Mobile Phases: A Review", J. Microcol. Sep., Volume 4, November 2, March/April 1992, p. 91–122, incorporated by reference. The modifier pump 501 introduces the modifier at a predetermined rate and pressure into the mixing tee 502 such that it mixes with the supercritical fluid without impeding its flow. Computer 64 and microprocessor 252 controls the modifier pump 501. Modifier pump 501 is added to the system as follows. Referring to FIG. 12, in a configuration without a modifier pump, a short piece of tubing 509 goes from on/off valve 506 to tee 508. Now referring to FIG. 20, when a modifier pump is plumbed into the system, tubing 509 is removed from between valve 506 and tee 508. A plumbing line 510 is then made to check valve 512. The purpose of check valve 512 is to prevent liquid modifier from back flowing from modifier pump 501 back to the $CO_2$ pump 34. Check valve 512 is plumbed to mixing tee 502. In mixing tee 502, the liquid modifier flow from pump 500 is mixed with the $CO_2$ flow from pump 34. The mixed $CO_2$/modifier flow is delivered through tube 514 to tee 508 and thus to the rest of the system. A plurality of modifier pumps in parallel could be plumbed to tee 502 to obtain tertiary and quaternary solvent mixtures. Also a dual headed, triple headed, or 4 headed modifier pump, as commonly used in liquid chromatography, could be used to delivery multi-component liquid modifier flow to the mixing tee 502 to mix with the $CO_2$ flow from pump 34.

In sample preparation strategies requiring the extraction of fat in foods, for example, certain challenges associated with the nature of the food matrix need to be addressed. One of these is the moisture content in foods. Certain foods can have high levels of moisture (up to 80%). Since both moisture and fat are extracted simultaneously by SFE, foods with low levels of moisture (<2%) can be extracted directly. However, samples with high moisture levels need to be pretreated prior to SFE as described previously to enhance the precision and accuracy of the extraction. One type of pre-treatment method involves purging an inert gas purge (such as nitrogen) through the food matrix in the extraction vessel prior to the extraction.

Referring to FIG. 12, the gas purge system 550 consists of an inert gas supply, such as nitrogen 552, that flows to an inlet on/off valve 554, and then to a tee 556. Tee 556 is plumbed into the vent line 558 between port 58 of valve 36 and another on/off valve 560. In operation, valve 40 is in its dynamic state, valve 38 is in its "A" position, valve 36 is controlled in its vent state, valve 560 is closed and valve 554 is open. Inert gas from the source flows at a pressure of 20 to 300 psi, and preferably 100 psi, through the plumbing and through vessel 30 to purge the matrix in vessel 30 of water.

The purge gas and water flows through the plumbing through restrictor 22 and into collection bottle 42. Alternatively, valve 38 can be switched to its "B" position to purge the water from the matrix in vessel 32.

The gas purge functions to displace the water content while keeping the sample heated to 100° C. and without any loss of fat or lipid components. After the gas purging, valve 554 is closed and valve 560 is opened, and then the extraction system operates as previously described to allow the carbon dioxide into the extraction vessel to perform the SFE process.

Since the determination of fats in foods by SFE can be a gravimetric procedure (weight loss), fat content is determined by weighing the vessel after the gas purging and then after the extraction. The following table illustrates the effect of the gas purging of pizza crust samples which contain 20–30% water and 17–36% fat. With the gas purging, SFE was able to achieve the target fat value (based upon Soxhlet extractions) with relative standard deviations less than 0.5%.

SFE of High Moisture Samples
(Pizza Crust - 20–30% water, 17.36% fat)

| Replicate | % Fat without gas purge | Replicate | % Fat with gas purge |
| --- | --- | --- | --- |
| 1 | 22.76 | 1 | 17.19 |
| 2 | 16.44 | 2 | 17.25 |
| 3 | 25.84 | 3 | 17.56 |
| 4 | 19.98 | 4 | 17.34 |
| 5 | 13.23 | 5 | 17.11 |
| 6 | 20.11 | 6 | 17.60 |

Examples utilizing the apparatus 10 now follow.

For the fat in food determinations, the most expeditious method utilized was by monitoring the gravimetric weight loss of the sample. This was accomplished by weighing the sample (inside the extraction vessel) on an analytical balance before and after the SFE procedure. Collection of the extracted fat analytes was not a concern, which allowed for performing faster extractions at high fluid flow rates. For these particular samples, the basic assumption was that all of the weight loss of the food sample was due to the extracted fat. This was validated by correlating SFE results with the conventional Soxhlet extraction data base for the chosen food samples. For the particular samples that were extracted in this study, the moisture content, as determined by the food manufacturer, was low (<2%), which did not substantially inflate the fat measurements. Moreover, each of the samples were heated for a period of time after the SFE run to liberate the $CO_2$ that became entrapped during the actual pressurization of the food sample. The food samples that were extracted included animal feed (corn and soybean) and potato chips as well as popcorn. All of these samples were characterized by classical Soxhlet liquid solvent extraction techniques prior to SFE.

Figure 4:
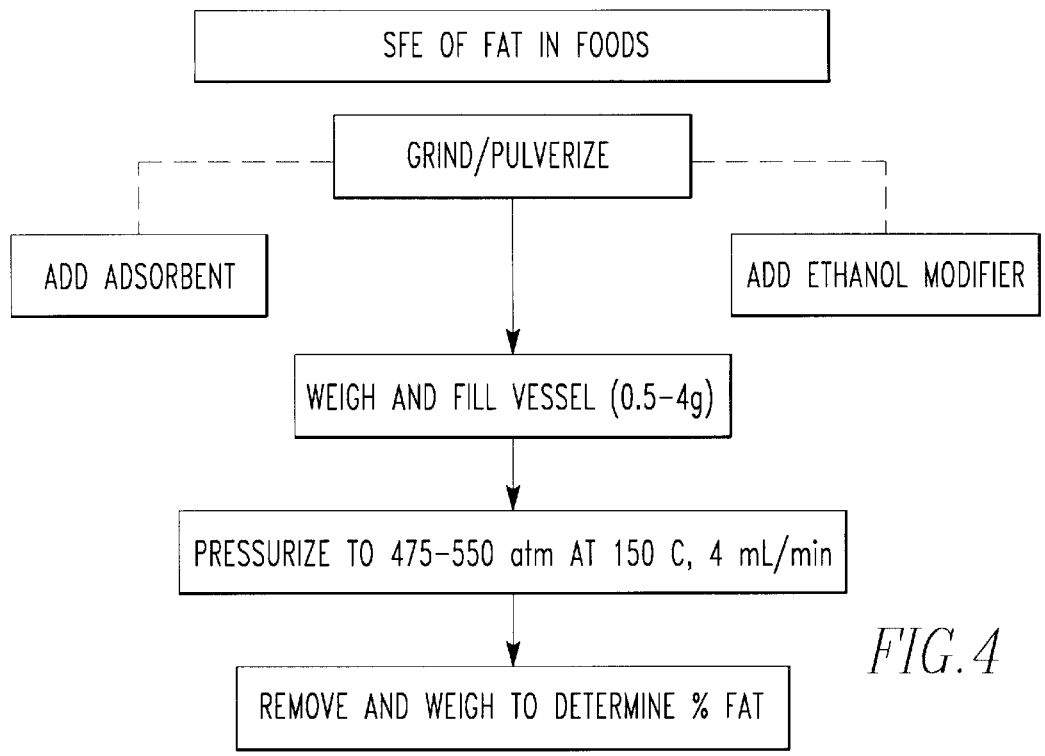
FIG. 4 is a block diagram of the procedure followed for fat extraction from food.
Figure 5:
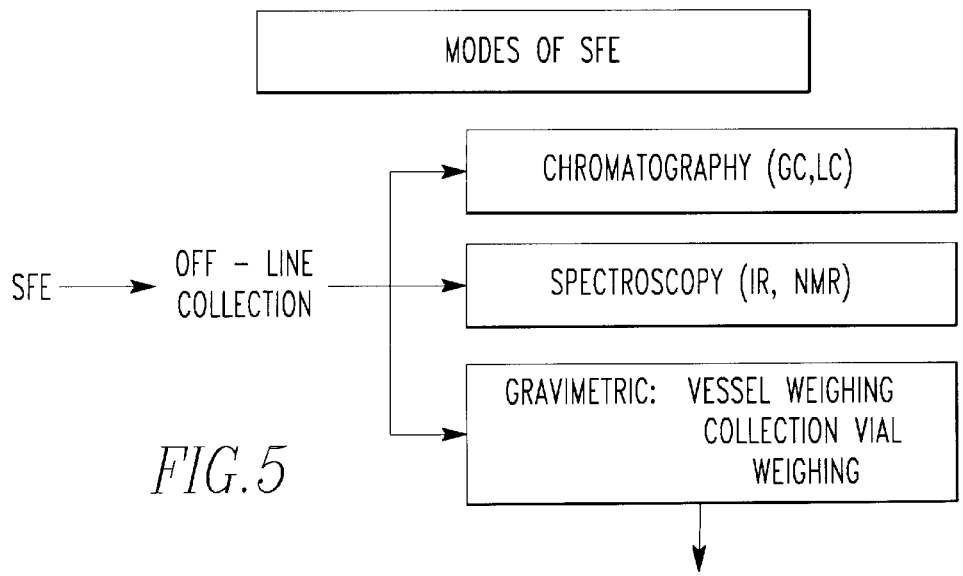
FIG. 5 is a block diagram of a procedure followed for the extraction of fat from foods.

Generally, the procedure that was followed for the fat from food extractions is outlined in FIG. 4 and FIG. 5. After the food sample was ground or pulverized, the sample was weighed into a 3 or 5 ml extraction vessel which accommodated approximately 1 to 1.5 grams of sample (depending on sample density). For the potato chips and popcorn, adsorbent or ethanol modifier was not needed to complete the extraction. For food samples with high water content (>2%), an adsorbent such as Hydromatrix (diatomaceous earth) needs to be added to the sample or extraction vessel to retain the water and thereby assure greater method accuracy. Moreover, some sample matrices also require a modifier, such as ethanol, to enhance the extraction efficiencies.

Table I lists some of the different sample types that have been extracted by gravimetric based fat determinations. Table I also indicates some of the sample types that required modifier. In these cases, ethanol was added to the sample as it was loaded in the extraction vessel prior to the extraction at 10–30% levels. After weighing in the sample (adding modifier or adsorbent, if necessary), the vessel was sealed, put into the extraction oven, and then extracted at the conditions indicated in Table I.

There are three alternatives for adding modifier to the sample: 1) the modifier can be added directly to the extraction vessel by pipeting the modifier directly to the vessel; or 2) a separate modifier pump can be added to the system to work in conjunction with the carbon dioxide pump 34. In this alternative, the modifier pump separately pumps the user selected modifier with then blends with the $CO_2$ downstream of the $CO_2$ pump, but before the extraction vessel. Thus, the solvent flowing to the extraction vessel is a mixture of $CO_2$ and modifier at a percentage selected by the use. 3) a pre-mixed tank of $CO_2$ and modifier can be used with the extraction system so that the $CO_2$ pump actually pumps the mixture and delivers it to the rest of the system.

The samples were extracted two at a time in two separate vessels in a staggered sequential mode (as shown in FIG. 1). This allowed greater sample throughput since vessel A was held in the static extraction mode, while vessel B was undergoing dynamic extraction. At the end of the extraction, the vessels were automatically depressurized, but were heated an additional 10 minutes (post-heat mode) to purge the samples of any entrapped $CO_2$. After the post-heating and subsequent automatic cooling, the vessels were weighed again to determine the weight loss (i.e. percent oil).

One of the distinct advantages of SFE is the ability to collect the extracted analytes off-line after extraction with vaporization of the supercritical solvent (i.e., $CO_2$) into a gas. These collected analytes can then be used for further analytical determinations. Another similar use of off-line SFE is to perform gravimetric determinations that correspond to the sample weight loss by weighing the extraction vessels or the collection vials. This includes not only the extraction of fats in snack or animal foods, but also fats in infant formula, non-ionic surfactants in soaps/detergents, and oligomers/additives in polymers, plastics or rubber, as shown in FIG. 5.

Figure 6:
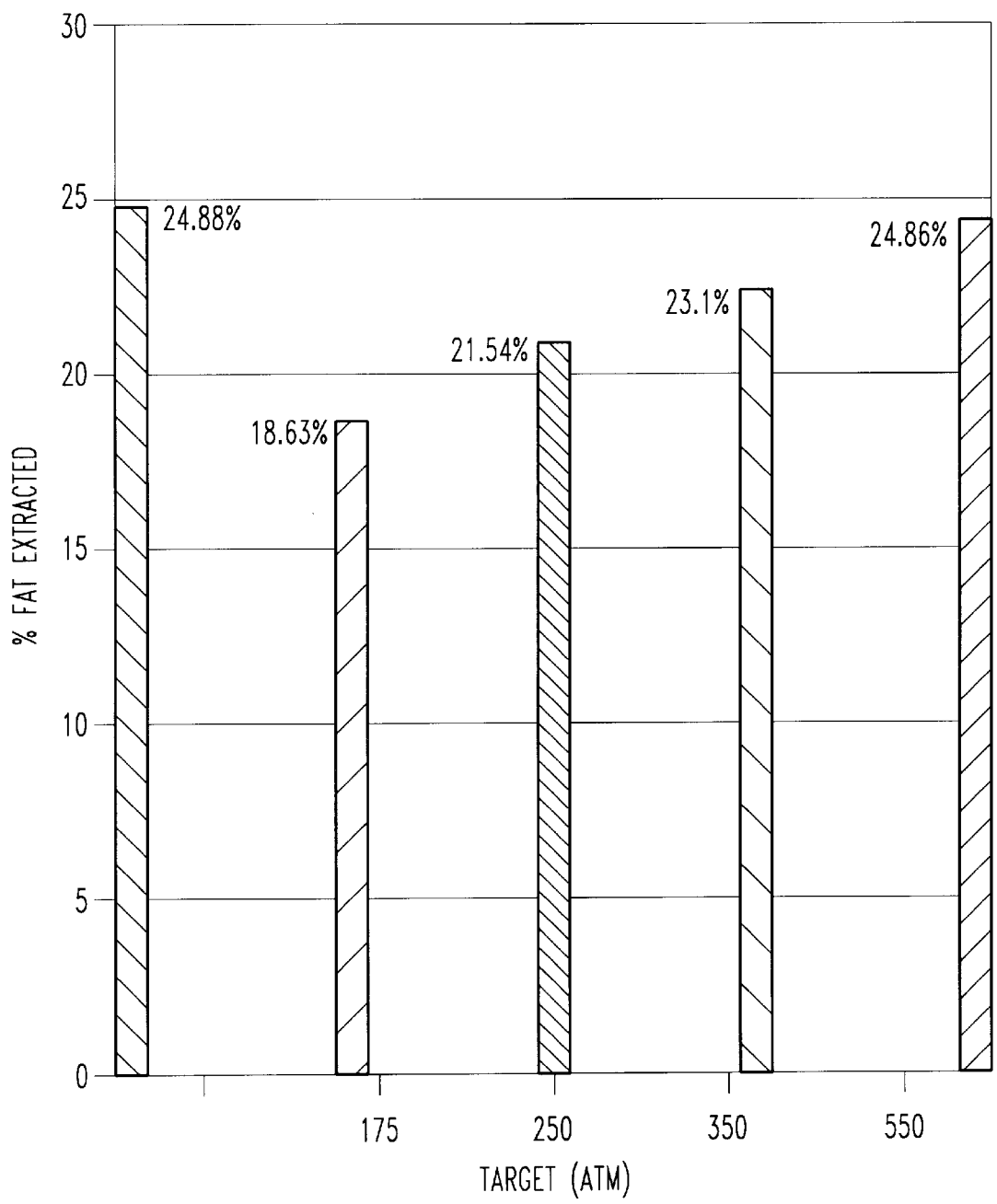
FIG. 6 is a graph of extraction pressure versus percent fat extracted from food.
Figure 7:
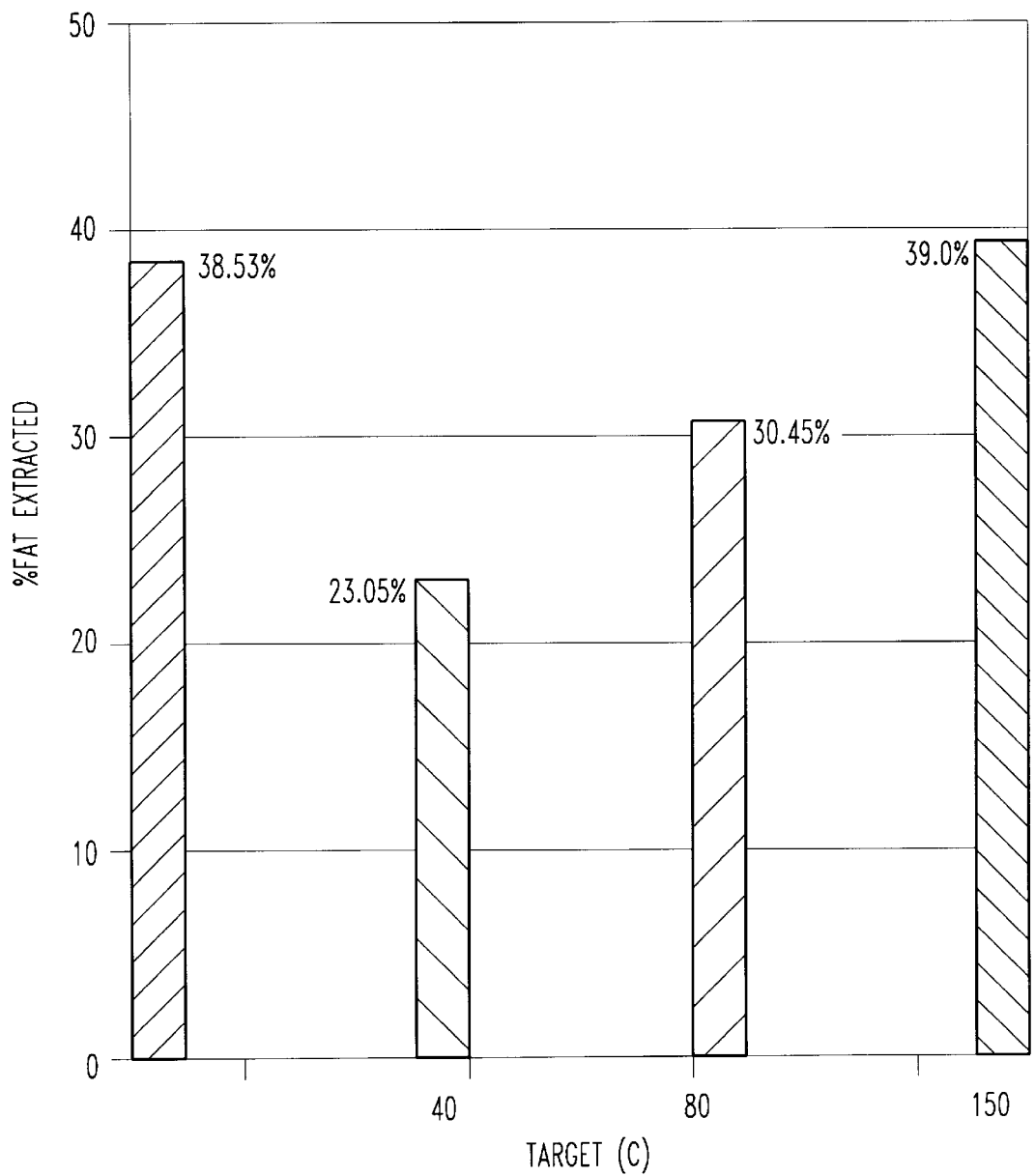
FIG. 7 is a graph of extraction temperature versus fat extraction from food.

In developing the SFE method for fat extraction, various operational parameters were tested to obtain high optimal extraction efficiencies in the shortest time possible. These parameters included pressure, temperature, flow rate and modifier concentration, which basically are the core extraction parameters for SFE. The results from optimizing extraction pressure for the determination of fat in a food product are shown graphically in FIG. 6. As the pressure was increased, the percent recovery increased to an optimum at 550 atm (as compared to the target Soxhlet value). No significant time savings were obtained when raising the pressure higher than 550 atm (i.e., 640 atm). The extraction temperature was another important parameter for the successful fat extraction in food products, as shown in FIG. 7. Significantly lower recoveries were obtained at 40° C. extraction temperatures with the optimum temperature being 150° C. without compromising sample integrity (i.e., physical charring of the sample). At temperatures above 150° C. (175° C.), some charring of the food products was noticed.

Figure 8:
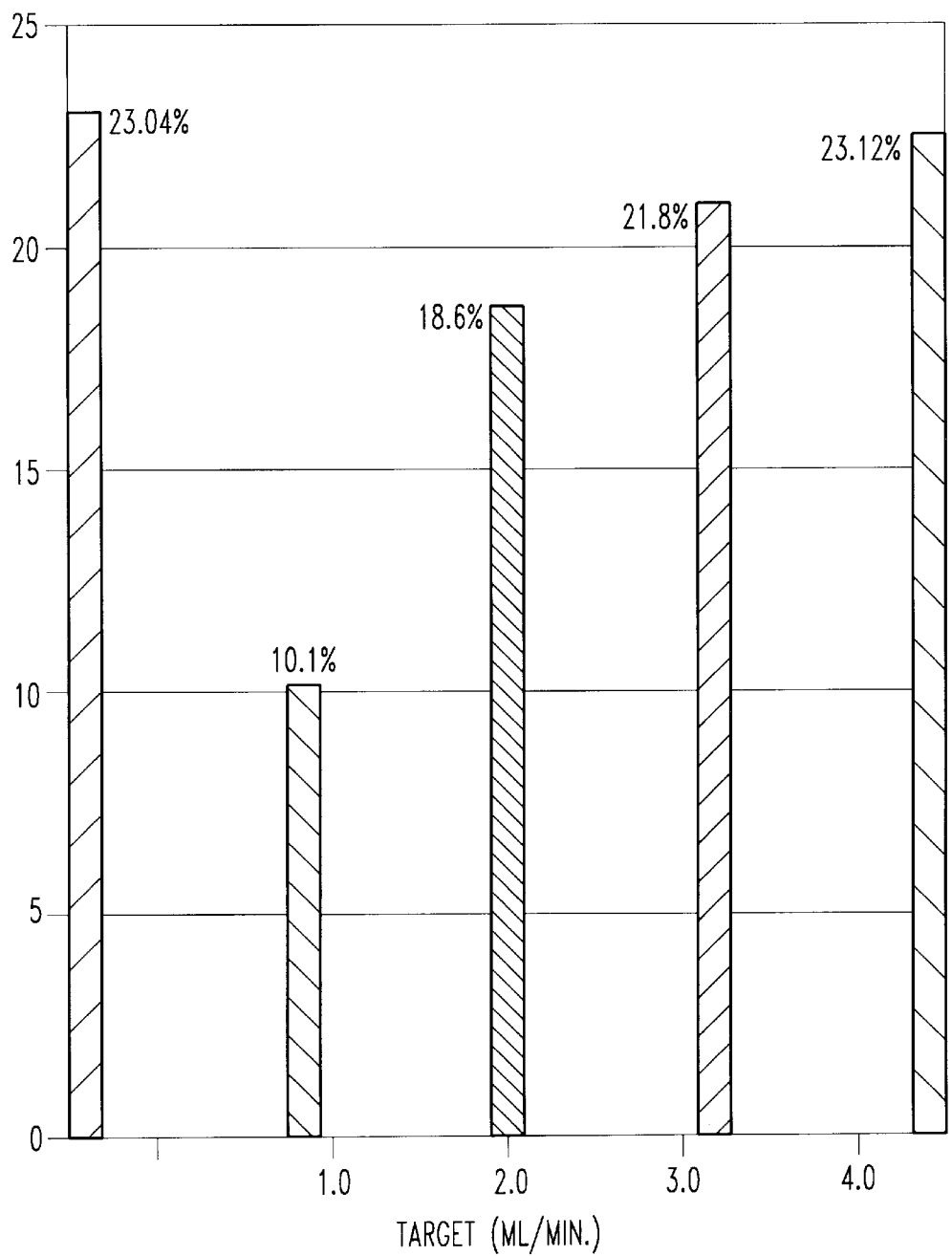
FIG. 8 is a graph of extraction fluid flow rates versus fat extraction from food.

Since the predominant mechanism for the extraction of fats from food products is dependent on fat solubility in the supercritical $CO_2$, faster extraction fluid flow rates should enhance extraction efficiencies. This is graphically shown in FIG. 8 for a food product. As the $CO_2$ flow rates were increased with the fixed extraction time, higher percent recoveries were obtained, since higher volumes of $CO_2$ were being exposed to the fat analytes in the food product matrix.

Figure 9:
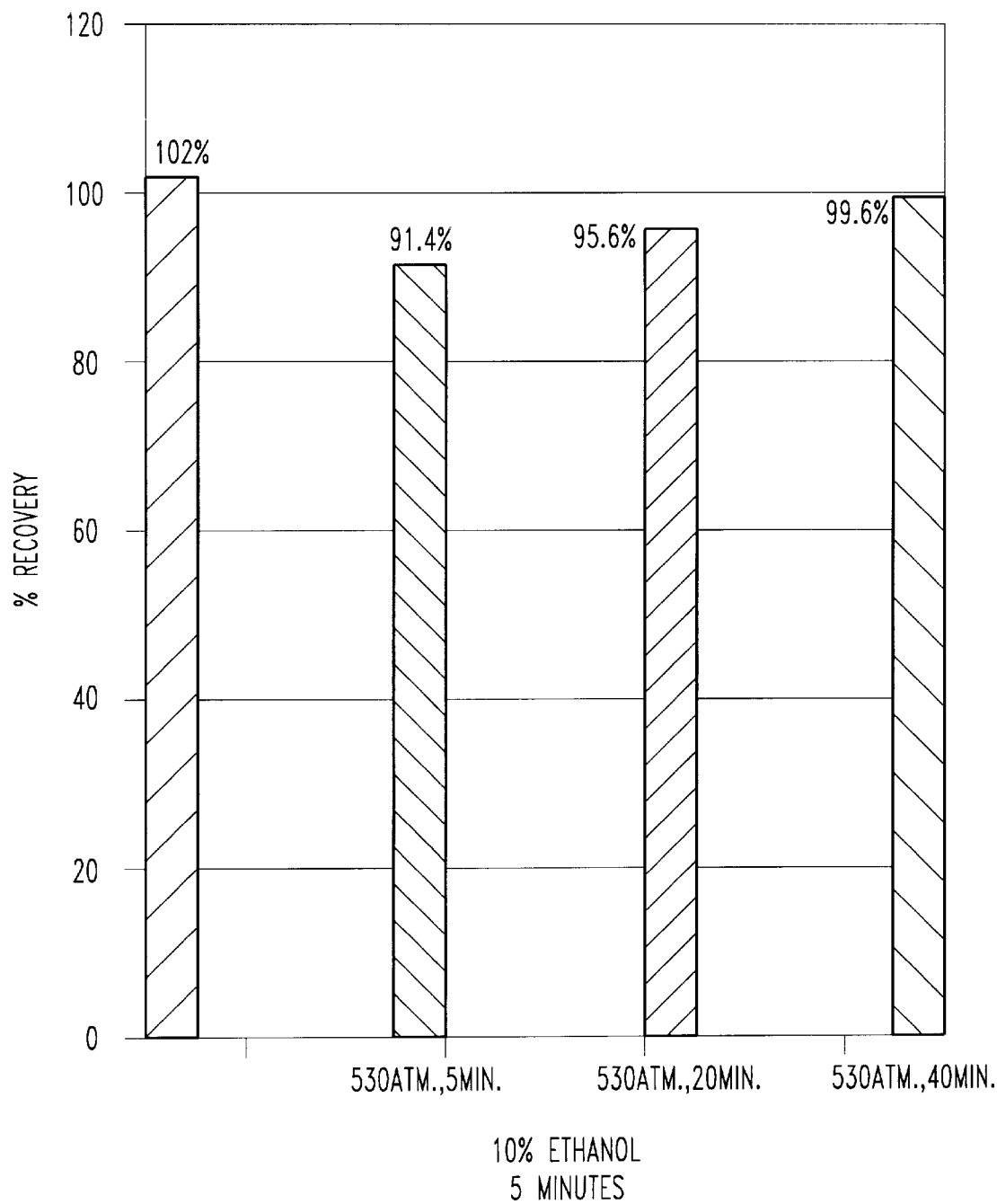
FIG. 9 is a graph of modifier in regard to pressure and time versus fat extraction recovery.

Finally, the effect of modifier on extraction efficiency, namely ethanol, was explored. Generally, extraction time can be shortened when using a modifier, either statically (modifier added to the extraction vessel) or dynamically (modifier pumped during the run). Moreover, using modifiers generally allows the use of lower SFE pressures while yielding high extraction efficiencies. An example of the use of modifier is shown in FIG. 9 with the SFE of fat in cheddar popcorn. As a function of extraction time, the percent recoveries of fat increased with the longer extraction time at the extraction pressure of 530 atm. Compared to the 40 minute extraction with pure $CO_2$, however, the use of 5% ethanol modifier decreased the extraction time to 5 minutes with equivalent recoveries.

Figure 10:
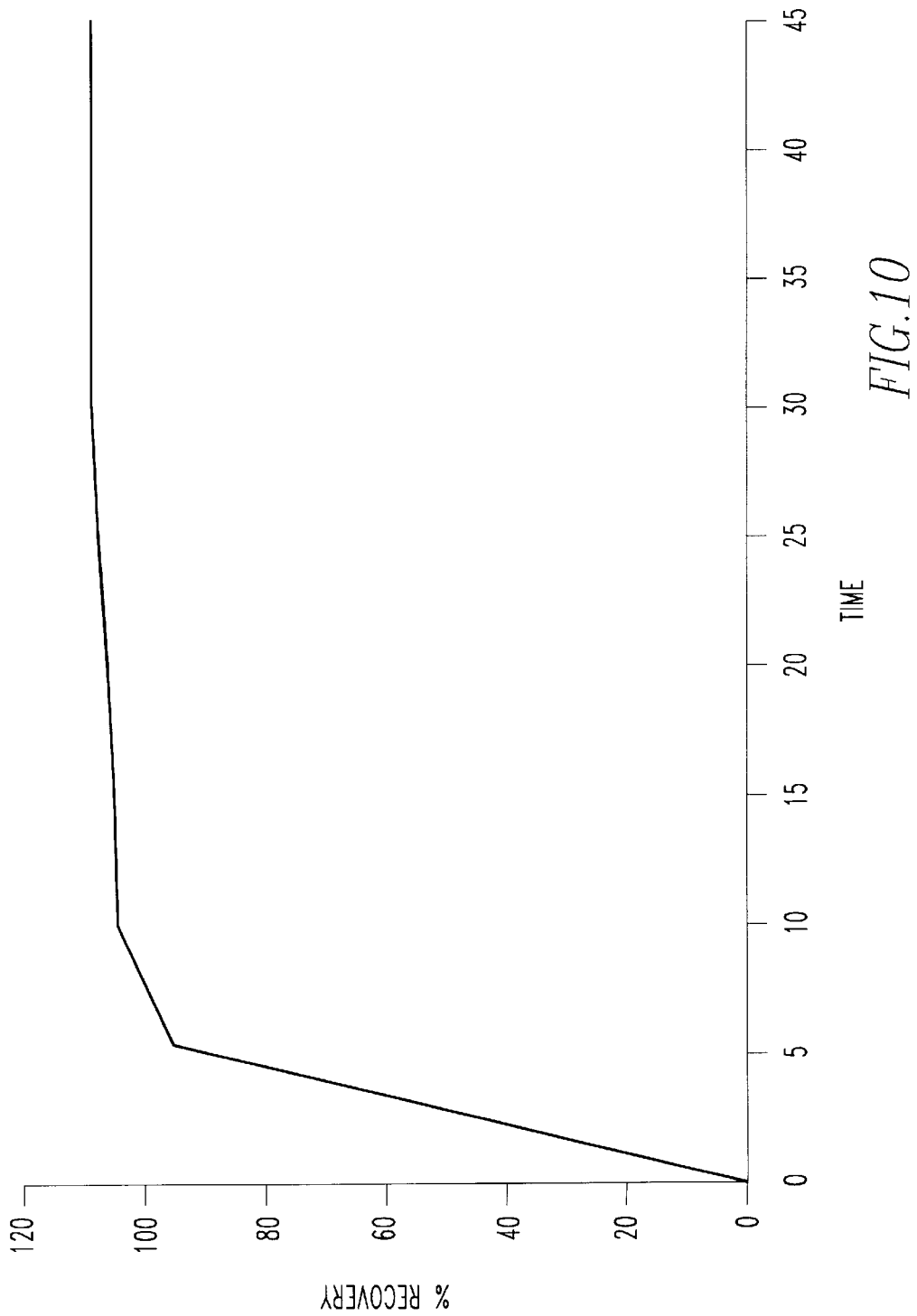
FIG. 10 is a graph of a fat extraction profile where extraction time is a function of profile recovery.

An example of a fat extraction profile where extraction time as a function of percent recovery was generated, is shown in FIG. 10 for potato chips. The SFE operating conditions were 550 atm, 150° C., 4 ml/minute compressed fluid flow and 35 minutes of repetitive step-wise static/dynamic extraction. Each of the points on the graph represents an average of three determinations using separate corn chip samples (as opposed to the same sample extracted progressively). Most of the fat (85%) is extracted within the first five minutes into the SFE run. However, additional time is needed to efficiently extract all of the fat from the sample. From a quality control perspective, this is an important point for food plants, especially when trending the data against the historical Soxhlet results.

After optimization of the key SFE operational parameters, a series of different food matrices were surveyed to demonstrate the applicability of the method and its precision, as well as viability for the replacement of Soxhlet extraction with SFE. The data from this survey is summarized in Table III, which compares the gravimetric determination of fat (oil) by SFE with Soxhlet extractions for different potato chip and popcorn matrices. The average SFE recoveries of fat from all of these foods was 98%–100%, with relative standard deviations ranging from 0.11% to 1.10% for ten replicates. For all of these food products, the SFE results correlated well with the Soxhlet data.

The key to the establishment of a routine SFE method is the operation and reliability of the restrictor. Historically, restrictor flow inhibition problems have plagued SFE (and SFC). Recently, advances in decompression mechanics, specifically in automatic variable restrictors, have eliminated many of these problems and have helped in advancing the ease of use of analytical SFE technology in general. Moreover, the SFE of fat from food presented a challenge for maintaining plug-free restrictor flow for the entire duration of the SFE run, due to the large amounts (milligram quantities) of fat that are extracted from some of the foods. Using the automated variable restrictor, these inhibitions to flow were eliminated. This is because the restrictor flow is continuously monitored and automatically maintained. Table IV lists the results of performing 25 continuous extractions of potato chips on the automated SFE using the variable restrictor under the following conditions: 475 atm, 150° C., 30 minutes of step-wise repetitive static/dynamic extraction and 4 ml/minute of compressed fluid flow. For these sequential extractions, a relative standard deviation of 0.45% was obtained for the potato chip samples.

Besides the advantages associated with sample throughput, automating SFE provides the additional capability to automatically optimize various extraction or collection parameters. This can be done by loading several extraction vessels with the sample matrix of interest, and then systematically varying one extraction parameter at a time. An example of this operation is shown in Table V for an automated method development scheme for the SFE of fats (oils) from corn and soybean based animal feeds. The recovery data presented here represents a series of twenty-one consecutive extractions that were performed with the SFE conditions that are identified for the three different animal feeds. Based upon the Soxhlet data, the SFE percent recoveries were significantly elevated when the ethanol modifier was used (compared to pure $CO_2$), and were in closer agreement to the target Soxhlet values using pure $CO_2$ at lower fluid flow rates.

The actual determination of fat is a gravimetric analysis, meaning that the user takes an extraction vessel, weights the empty extraction vessel on an analytical balance and record the weight; the user fills the vessel with the matrix to be determined (e.g. a snack food with some x% fat content); and then weights the vessel and matrix to obtain the weight of the matrix:

$$\begin{array}{c}\text{Weight of matrix} \\ \text{before extraction}\end{array} = \begin{array}{c}\text{weight of vessel and} \\ \text{matrix before extraction}\end{array} - \begin{array}{c}\text{weight of empty} \\ \text{vessel}\end{array}$$

The user loads the vessel into the extraction system and performs an extraction (like doing the method in Table 2). After the extraction is completed, all of the fat that was in the sample has been extracted. The user takes the extraction vessel out of the system and re-weights the vessel and obtains the % fat by the equations:

$$\begin{array}{c}\text{Weight of matrix} \\ \text{after extraction}\end{array} = \begin{array}{c}\text{weight of vessel and} \\ \text{matrix after extraction}\end{array} - \begin{array}{c}\text{weight of empty} \\ \text{vessel}\end{array}$$

$$\% \text{ fat} = \frac{\text{Weight of matrix after extraction}}{\text{Weight of matrix before extraction}} \times 100$$

The SFE extraction also extracts the water from the matrix (as does Soxhlet extraction). Thus the % fat value must be corrected for the % water in the matrix. This can be done by 1) a separate water determination on the sample and then correcting the results for the water content, or 2) drying the sample before SFE extraction so that there is no water to correct for, 3) by adding a drying agent, such as Hydromatrix (a diatomaceous earth) directly to the vessel and matrix to absorb the water and thus the SFE step will not extract the water from the Hydromatrix, or 4) performing an inert gas purge on the matrix to drive off the water.

TABLE 1

Use of SFE for Gravimetric Fat Determinations

| Matrix | Sample Wt | Pressure (atm) | Temp (° C.) | Flow (ml/min) Compressed | Time (min) | % Recovery |
|---|---|---|---|---|---|---|
| Popcorn | 3 g | 475 | 150 | 4.0 | 15 | 100 |
| Animal Feed | 1 g | 350 | 40 | 4.0 | 20 | 100 |
| Snack Crackers | 1 g | 475 | 150 | 4.0 | 20 | 100 |
| Infant Formula | 4 g | 475 | 150 | 3.5 | 60 | 100 |
| Soybeans* | 2 g | 475 | 150 | 4.0 | 30 | 98 |
| Soybean Flakes | 2 g | 640 | 80 | 6.0 | 60 | 100 |

TABLE 1-continued

Use of SFE for Gravimetric Fat Determinations

| Matrix | Sample Wt | Pressure (atm) | Temp (° C.) | Flow (ml/min) Compressed | Time (min) | % Recovery |
|---|---|---|---|---|---|---|
| Wheat Germ* | 2 g | 475 | 150 | 4.0 | 30 | 98 |
| Potato Chips | 2 g | 475 | 150 | 4.0 | 30 | 99 |
| Tortilla Snacks | 2 g | 550 | 150 | 4.0 | 20 | 100 |
| Cheese Snacks | 1.5 g | 475 | 150 | 4.0 | 15 | 100 |
| Corn Snacks | 1.5 g | 550 | 150 | 4.0 | 35 | 100 |

*10–30% Ethanol added directly to vessel before SFE

TABLE 2

Tortilla Chips Manual Dual Vessel SFE Method Steps

|  | Valve 1* | Valve 2** | Time | ATM | ° C. | Valve 3 |
|---|---|---|---|---|---|---|
| EQUILIBRATE | ST | A |  | 550 | 150 | Vent |
| 1 | DY | A | 5.00 | 550 | 150 | PM |
| 2 | DY | B | 10.00 | 550 | 150 | PM |
| 3 | DY | A | 10.00 | 550 | 150 | PM |
| 4 | DY | B | 5.00 | 550 | 150 | PM |
| 5 | ST | A | 0.50 | 550 | 150 | Vent |
| 6 | ST | B | 0.50 | 550 | 150 | Vent |
| 7 | ST | A | 5.00 | 550 | 150 | Vent |
| 8 | ST | B | 5.00 | 550 | 150 | Vent |

*ST: Static, DY: Dynamic
**Vessel A and Vessel B

TABLE 3

Correlation of SFE with Soxhlet for Fat in Food Products

| Product | Mean % Oil | % Recovery | Standard Deviation | % RSD | N | Technique |
|---|---|---|---|---|---|---|
| Potato | 39.99 |  | 0.176 | 0.44 | 5 | Soxhlet |
| Chips A | 39.80 | 99.5% | 0.099 | 0.25 | 10 | SFE |
| Potato | 21.67 |  | 0.26 | 1.2 | 5 | Soxhlet |
| Chips B | 21.65 | 100% | 0.099 | 0.46 | 10 | SFE |
| Barbecue | 38.31 |  | 0.406 | 1.0 | 5 | Soxhlet |
| Potato Chips | 37.71 | 98% | 0.109 | 1.10 | 10 | SFE |
| Corn | 31.58 |  | 0.63 | 2.0 | 5 | Soxhlet |
| Chips | 31.02 | 98% | 0.034 | 0.11 | 10 | SFE |
| Nacho | 26.34 |  | 0.17 | 0.645 | 5 | Soxhlet |
| Tortilla Chips | 26.12 | 99% | 0.043 | 0.165 | 10 | SFE |
| Cheese | 26.89 |  | 0.488 | 1.81 | 5 | Soxhlet |
| Tortilla Chips | 26.40 | 98% | 0.122 | 0.462 | 10 | SFE |
| Cheese Snacks | 32.33 |  | 0.284 | 0.88 | 5 | Soxhlet |
|  | 32.13 | 99% | 0.121 | 0.37 | 10 | SFE |
| Buttered | 34.80 |  | 0.063 | 0.18 | 5 | Soxhlet |
| Popcorn | 34.43 | 99% | 0.053 | 0.15 | 10 | SFE |
| Cheese | 40.76 |  | 0.97 | 2.4 | 5 | Soxhlet |
| Popcorn | 40.22 | 98% | 0.14 | 0.35 | 10 | SFE |

Reproducibility Testing of Automated SFE for Fat in Potato Chips Replicate Extractions - Gravimetric Results
Percent Fats*

| 17.25 | 17.84 | 17.85 | 17.76 | 17.65 |
|---|---|---|---|---|
| 17.46 | 17.56 | 17.77 | 17.56 | 17.17 |
| 17.65 | 17.10 | 17.63 | 17.33 | 17.97 |
| 17.21 | 17.01 | 17.36 | 17.13 | 17.86 |
| 17.84 | 17.85 | 17.77 | 17.87 | 17.77 |

Mean: 17.67%
Standard Deviation: 0.17%
% RSD: 0.45%

*Target Value: 17.86%

TABLE 5

Automated SFE Method Development for the Determination of Fat (Oils) in Animal Feeds (Gravimetric Procedure)

| | PERCENT RECOVERY | | |
|---|---|---|---|
| | Corn Feed #1 | Soybean Feed #2 | Corn Feed #3 |
| 475 atm/40° C./10% Ethanol/ 2.5 ml/min. (.99 g/ml) | 26.86 | 21.41 | 30.34 |
| 475 atm/150° C./10% Ethanol/ 2.5 ml/min. (.69 g/ml) | 30.14 | 28.61 | 33.03 |
| 475 atm/40° C./2.5 ml/min. (.99 g/ml) | 12.15 | 11.62 | 14.12 |
| 475 atm/150° C./2.5 ml/min. (.69 g/ml) | 14.15 | 12.14 | 18.67 |
| 400 atm/40° C./2.5 ml/min. (.96 g/ml) | 8.42 | 6.11 | 9.11 |
| 350 atm/40° C./2.0 ml/min (.94 g/ml) | 2.01 | 1.26 | 3.00 |
| 350 atm/40° C./4.0 ml/minute | 2.74* | 1.47* | 3.40* |

*Optimized conditions based upon the following Soxhlet based values:
Corn Feed #1 2.7%
Soybean Feed #2 1.5%
Corn Feed #3 3.5%

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A restrictor for flow of supercritical solvent comprising:
    a housing having a central chamber and a first port, second port and third port connected to the central chamber;
    a high pressure tube connected to the first port which delivers supercritical solvent to the chamber through the first port;
    an actuator mechanism connected to the second port;
    a needle connected to the actuator mechanism, said needle extending from the actuator mechanism through the chamber and through the third port, said actuator mechanism moving the needle to maintain a desired flow of supercritical solvent out the third port and compensating for flow rate error due to temperature effects, said needle having a needle end; and
    an outlet tube which is connected to the third port and extends from the third port, said outlet tube surrounding the needle, said outlet tube having an opening which conforms with the needle and to control the flow of solvent out the third port and the change in pressure of the solvent, said needle end and outlet tube opening remote from the housing.

2. A restrictor as described in claim 1 including a solvent flush mechanism connected to the third port to provide solvent flush to the chamber and third port to clear them of solvent.

3. A restrictor as described in claim 2 wherein the housing includes a fourth port; and including a solvent flush mechanism connected to the fourth port to provide solvent flush to the chamber and third port to clear them of solvent and analyte.

4. A restrictor as described in claim 3 including a heating mechanism adjacent to the needle end and the tube outlet opening to heat the outlet opening and needle end so solvent or analyte does no t clog the outlet tube opening.

5. A restrictor as described in claim 4 wherein the solvent flush mechanism includes solvent flush tubing connected to the fourth port of the housing, and a solvent flush pump connected to the tubing to pump the solvent flush to the fourth port.

6. A restrictor as described in claim 5 wherein the solvent flush mechanism includes a solvent flush check valve disposed in the solvent flush tubing to prevent solvent from the first port flowing through the solvent flush tubing, said solvent flush check valve disposed between the housing and the solvent flush pump; and a solvent flush supply connected to the solvent flush pump.

7. A restrictor as described in claim 6 wherein the actuator mechanism includes an actuator, and including a control mechanism for controlling the movement of the actuator to move the needle end relative to the outlet opening.

8. A restrictor as described in claim 7 including a ferrule disposed in the second outlet between the actuator and the chamber, said needle extending through said ferrule, said ferrule sealing the second outlet so solvent from the first outlet cannot flow in to the second outlet.

9. A restrictor as described in claim 8 wherein the control mechanism includes a motor mechanism to move the actuator to move the needle and a computer mechanism for instructing the motor mechanism how to move the actuator to move the needle, said computer mechanism connected to the solvent flush pump to control when the solvent pump operates.

10. A restrictor as described in claim 9 wherein the motor mechanism includes a stepper motor connected to the actuator to move the actuator, and a stepper motor driver connected to the stepper motor and to control mechanism to drive the stepper motor.

11. A restrictor as described in claim 10 wherein the control mechanism includes a computer to determine how to move the actuator, and a central microprocessor connected to the stepper motor driver and the solvent flush pump for controlling their operation.

12. A restrictor as described in claim 11 wherein the solvent flush is methanol, methylene chloride, acetone or hexane.

13. A restrictor as described in claim 12 wherein the heating mechanism includes an inductive heating mechanism, a cartridge heater providing conductive heat, a hot air convection heater, or a microwave heater.

14. A restrictor as described in claim 7 wherein the needle end is flared radially outward from the needle axis, and the outlet tube opening has a shape which conforms with the flared end of the needle end.

15. A restrictor as described in claim 7 wherein the needle end is a point and the point defines a seating surface, and the outlet tube opening conforms with the point of the needle end, said outlet tube opening defined by an outlet tube seating surface on the interior of the outlet tube.

16. A restrictor as described in claim 1 including a collector connected to the outlet tube opening.

17. A restrictor as described in claim 16 wherein the collector is comprised of an analyte trap, a solvent trap, or a waste vial.

18. A restrictor as described in claim 1 including a chromatograph having an inlet port to which the outlet tube is connected.

19. A restrictor as described in claim 18 wherein the chromatograph is a gas, liquid or supercritical chromatograph.

20. A restrictor as described in claim 1 including an infrared detection device or a mass spectrometer which is coupled to the outlet tube.

21. A restrictor for flow of supercritical solvent comprising:

a housing having a central chamber and a first port, second port and third port connected to the central chamber;

a high pressure tube connected to the first port which delivers supercritical solvent to the chamber through the first port;

an actuator mechanism connected to the second port, said actuator mechanism includes an actuator and a control mechanism;

a needle connected to the actuator mechanism, said needle extending from the actuator mechanism through the chamber and through the third port, said actuator mechanism moving the needle to maintain a desired flow of supercritical solvent out the third port, said needle having a needle end; and an outlet tube which is connected to the third port and extends from the third port, said outlet tube surrounding the needle, said outlet tube having an opening which conforms with the needle and to control the flow of solvent out the third port and the change in pressure of the solvent, said needle end and outlet tube opening remote from the housing, said control mechanism for controlling the movement of the actuator to move the needle end relative to the outlet opening, the control mechanism includes a motor mechanism to move the actuator to move the needle and a computer mechanism for instructing the motor mechanism how to move the actuator to move the needle, said motor mechanism includes a stepper motor connected to the actuator to move the actuator, and a stepper motor driver connected to the stepper motor and to the control mechanism to drive the stepper motor, said control mechanism includes a computer to determine how to move the actuator, and a central microprocessor connected to the stepper motor driver for controlling the driver's operation.

22. A restrictor for flow of supercritical solvent comprising:

a housing having a central chamber and a first port, second port and third port connected to the central chamber;

a high pressure tube connected to the first port which delivers supercritical solvent to the chamber through the first port;

an actuator mechanism connected to the second port;

a needle connected to the actuator mechanism, said needle extending from the actuator mechanism through the chamber and through the third port, said actuator mechanism moving the needle to maintain a desired flow of supercritical solvent out the third port, said needle having a needle end and a needle axis, said needle end flared radially outward from the needle axis; and an outlet tube which is connected to the third port and extends from the third port, said outlet tube surrounding the needle, said outlet tube having an opening which conforms with the needle and to control the flow of solvent out the third port and the change in pressure of the solvent, said needle end and outlet tube opening remote from the housing, said outlet tube opening has a shape which conforms with the flared end of the needle end.

* * * * *